(12) United States Patent
Long et al.

(10) Patent No.: US 7,116,414 B2
(45) Date of Patent: Oct. 3, 2006

(54) ON-LINE MEASUREMENT AND CONTROL OF POLYMER PROPERTIES BY RAMAN SPECTROSCOPY

(75) Inventors: Robert L. Long, Houston, TX (US); David G. Marrow, Taylor Lake Village, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 186 days.

(21) Appl. No.: 10/492,442

(22) PCT Filed: Oct. 15, 2002

(86) PCT No.: PCT/US02/32767

§ 371 (c)(1), (2), (4) Date: Apr. 13, 2004

(87) PCT Pub. No.: WO03/042646

PCT Pub. Date: May 22, 2003

(65) Prior Publication Data

US 2004/0233425 A1    Nov. 25, 2004

Related U.S. Application Data

(60) Provisional application No. 60/345,337, filed on Nov. 9, 2001.

(51) Int. Cl.
*G01J 3/44* (2006.01)
(52) U.S. Cl. ..................... 356/301
(58) Field of Classification Search ............... 356/301
See application file for complete search history.

(56) References Cited

U.S. PATENT DOCUMENTS 3,725,378 A    4/1973    Chamberlin 3,779,712 A    12/1973    Calvert et al.

(Continued)

FOREIGN PATENT DOCUMENTS

EP          238 796         9/1987

(Continued)

OTHER PUBLICATIONS

Ardell, G.G., et al.; "*Model Prediction for Reactor Control*", Amer. Institute of Chem. Eng., U.S., vol. 79, No. 6, Jul. 1, 1983, pp. 78-83, (ISSN 0360-7275).

(Continued)

*Primary Examiner*—Gregory J. Toatley, Jr.
*Assistant Examiner*—Kara Geisel
(74) *Attorney, Agent, or Firm*—Andrew B. Girffis

(57) ABSTRACT

Methods are provided for determining and controlling polymer properties on-line in a polymerization reactor system, such as a fluidized bed reactor. The methods include obtaining a regression model for determining a polymer property, the regression model including principal component loadings and principal component scores, acquiring a Raman spectrum of a polyolefin sample comprising polyolefin, calculating a new principal component score from at least a portion of the Raman spectrum and the principal component loadings, and calculating the polymer property by applying the new principal component score to the regression model. The property can be controlled by adjusting at least one polymerization parameter based on the calculated polymer property.

26 Claims, 11 Drawing Sheets

U.S. PATENT DOCUMENTS

| | | | |
|---|---|---|---|
| 4,175,169 A | 11/1979 | Beals et al. | |
| 4,182,810 A | 1/1980 | Willcox | |
| 4,243,619 A | 1/1981 | Fraser et al. | 264/40.06 |
| 4,469,853 A | 9/1984 | Mori | |
| 4,540,753 A | 9/1985 | Cozewith et al. | |
| 4,543,399 A | 9/1985 | Jenkins, III et al. | 526/70 |
| 4,588,790 A | 5/1986 | Jenkins, III et al. | 526/70 |
| 4,620,049 A | 10/1986 | Schmidt et al. | |
| 4,621,952 A | 11/1986 | Aronson | |
| 4,888,704 A | 12/1989 | Topliss et al. | |
| 5,096,634 A | 3/1992 | Tsadares et al. | |
| 5,121,337 A | 6/1992 | Brown | |
| 5,151,474 A | 9/1992 | Lange et al. | 526/60 |
| 5,202,395 A | 4/1993 | Chambon | |
| 5,270,274 A | 12/1993 | Hashiguchi et al. | |
| 5,274,056 A | 12/1993 | McDaniel et al. | |
| 5,352,749 A | 10/1994 | DeChellis et al. | 526/68 |
| 5,405,922 A | 4/1995 | DeChellis et al. | 526/68 |
| 5,436,304 A | 7/1995 | Griffin et al. | 526/68 |
| 5,462,999 A | 10/1995 | Griffin et al. | 526/68 |
| 5,589,555 A | 12/1996 | Zboril et al. | |
| 5,638,172 A | 6/1997 | Alsmeyer et al. | |
| 5,675,253 A | 10/1997 | Smith et al. | |
| 5,678,751 A | 10/1997 | Buchanan et al. | |
| 5,682,309 A | 10/1997 | Bartusiak et al. | |
| 5,696,213 A | 12/1997 | Schiffino et al. | |
| 5,751,415 A * | 5/1998 | Smith et al. | 356/301 |
| 5,864,403 A | 1/1999 | Ajji et al. | |
| 5,892,228 A | 4/1999 | Cooper et al. | |
| 5,999,255 A | 12/1999 | Dupee et al. | |
| 6,072,576 A | 6/2000 | McDonald et al. | |
| 6,095,982 A * | 8/2000 | Richards-Kortum et al. | 356/301 |
| 6,144,897 A | 11/2000 | Selliers | 700/269 |
| 6,204,344 B1 | 3/2001 | Kendrick et al. | |
| 6,204,664 B1 | 3/2001 | Sardashti et al. | |
| 6,218,484 B1 | 4/2001 | Brown et al. | 526/68 |
| 6,228,793 B1 | 5/2001 | Hosaka et al. | |
| 6,239,235 B1 | 5/2001 | Hottovy et al. | |
| 6,281,300 B1 | 8/2001 | Kendrick | |
| 6,380,325 B1 | 4/2002 | Kendrick | |
| 6,405,579 B1 | 6/2002 | Tjahjadi et al. | |
| 6,479,597 B1 | 11/2002 | Long et al. | |
| 6,673,878 B1 | 1/2004 | Donck | |
| 2002/0156205 A1 | 10/2002 | Long, et al. | |
| 2004/0198927 A1 | 10/2004 | Battiste | |
| 2004/0233425 A1 | 11/2004 | Long et al. | |
| 2004/0266959 A1 | 12/2004 | Heslop et al. | |
| 2005/0154155 A1 | 7/2005 | Battiste | |

FOREIGN PATENT DOCUMENTS

| | | | |
|---|---|---|---|
| EP | 257 316 A1 | 3/1988 | |
| EP | 257 316 B1 | 3/1988 | |
| EP | 328 826 | 8/1989 | |
| EP | 0 561 078 A2 | 9/1993 | |
| EP | 561 078 | 9/1993 | |
| EP | 406 805 | 12/1995 | |
| JP | 02038841 | 2/1990 | |
| WO | WO 94/21962 | 9/1994 | |
| WO | WO 96/41822 | 12/1996 | |
| WO | WO 98/08066 | 2/1998 | 21/65 |
| WO | WO 99/01750 | 1/1999 | |
| WO | WO 01/09201 A2 | 2/2001 | |
| WO | WO 01/09203 A1 | 2/2001 | |
| WO | WO 2004/063234 | 7/2004 | |
| WO | WO 2005/049663 | 6/2005 | |

OTHER PUBLICATIONS

K.R. Beebe et al., "*An Introduction to Multivariate Calibration and Analysis,*" Analytical Chemistry, vol. 59, No. 17, pp. 1007A-1017A, Sep. 1, 1987.

J.M. Tedesco et al., "*Calibration of dispersive Raman Process Analyzers,*" The Society Of Photo-Optical Instrumentation Engineers, vol. 3537, pp. 200-212, 1999.

G.A. Bakken et al., "*Examination of Criteria for Local Model Principal Component Regression,*" Society for Applied Spectroscopy, vol. 51, No. 12, pp. 1814-1822, 1997.

P. Erlich et al., "*Fundamentals of the Free-Radical Polymerization of Ethylene,*" Advanced Polymer Science, vol. 7, pp. 386-448, 1970.

M.L. Myrick et al., "*In Situ FIber-Optic Raman Spectroscopy of Organic Chemistry in a Supercritical Water Reactor,*" Journal of Raman Spectroscopy, vol. 25, pp. 59-65, 1994.

T. Naes et al., "*Locally Weighted Regression and Scatter Correction for Near-Infrared Reflectance Data,*" Analytical Chemistry, vol. 62, pp. 664-673, 1990.

J.J. Zacca et al., "*Modelling of the Liquid Phase Polymerization of Olefins in Loop reactors,*" Chemical Engineering Science, vol. 48, No. 22, pp. 3743-3765, 1993.

L.P. Russo et al., "*Moving-Horizon State Estimation Applied to an Industrial Polymererization Process,*" American Control Conf. Proc., San Diego, CA, 1999.

H. Martens et al., "*Multivariate Calibration,*" Wiley & Sons Ltd., pp. viii-ix, 1989.

*Multivariate Data Analysis for Windows—Version 3.0,* excerpted from Pirouette Software Manual, Exploratory Analysis: Principal Component Analysis, pp. 5-13 through 5-40, 1985-2000.

E.P.C. Lai et al., "*Noninvasive Spectroscopic Detection of Bulk Polymerization by Stimulated Raman Scattering,*" Applied Spectroscopy, vol. 48, No. 8, 1994.

S. Sekulic et al., "*Nonlinear Multivariate Calibration Methods in Analytical Chemistry,*" Analytical Chemistry, vol. 65, No. 19, pp. 835A-845A, Oct. 1, 1993.

E.D. Lipp et al., "*On-Line Monitoring Of Chlorosilane Streams By Raman Spectroscopy,*" Reprinted from Applied Spectroscopy, vol. 52, No. 1, Jan. 1998.

D.R. Battiste et al., "*On-Line Raman Analysis of Ethylene and Hexene in the Phillips 1-Hexene and Polyethylene Processes,*" Gulf Coast Conference presentation (Abstract).

M.J. Pelletier et al.; "*Optical fibers enable Raman instruments to analyze industrial process problems quickly and accurately,*" Raman Spectroscopy—Keeps Industry Under Control, Reprint: Photonics Spectra, 4 pgs. Oct. 1997.

V. Centner et al., "*Optimization in Locally Weighted Regression,*" Analytical Chemistry, vol. 70, No. 19, pp. 4206-4211, Oct. 1, 1998.

"*Principal Components Analysis,*" excerpted from PLS_Toolbox, Version 2.0 Data Analysis Manual, Eigenvector Research, Inc., pp. 32-34, 1998.

L. Markwort et al., "*Raman Imaging of Heterogeneous Polymers: A Comparison of Global versus Point Illumination,*" Applied Spectroscopy, vol. 49, No. 10, pp. 1411-1430, 1995.

I. Modric et al., "*Raman- und Infrarotspektren isotaktischer Polyalkylathylene*,*" Colloid & Polymer Sci., vol. 254, pp. 342-347, 1976.

M.G. Hansen et al., "*Real-Time Monitoring of Industrial Polymers,*" Raman Review; pp. 1-4, Mar. 1998.

S.E. Nave "*Rugged Fiber Optic Probes and Sampling Systems for Remote Chemical Analysis Via the Raman Technique,*" ISA, Paper #96-042, pp. 453-467, 1996.

M.J. Pelletier et al., "*Shining a Light on Wet Process Control,*" Semiconductor International, 4 pages, Mar. 1996.

K.P.J. Williams et al., "*Use of Micro Raman Spectroscopy for the Quantitative Determination of Polyethylene Density Using Partial Least-Squares Calibration,*" Journal of Raman Spectroscopy, vol. 26, pp. 427-433, 1995.

J.M. Tedesco et al., "Calibration of dispersive Raman process analyzers," Part of the SPIE Conference on Online Chemical Process Monitoring w/Advanced Techniques, SPIE, vol. 3537, pp. 200-212, Nov. 1998.

A.C. Ouano et al., "Gel Permeation Chromatography," Polymer Molecular Weights Part II, Chapter 6, pp. 287-378, 1975.

Verstrate et al., "Near Monodisperse Ethylene-Propylene Copolymers by Direct Ziegler-Natta Polymerization. Preparation, Characterization, Properties," Macromolecules, vol. 21, pp. 3360-3371, 1988.

F. Rodriguez, "Principles of Polymer Systems 3rd Ed.," Hemisphere Pub. Corp., NY, pp. 155-160, 1989.

* cited by examiner

ON-LINE MEASUREMENT AND CONTROL OF POLYMER PROPERTIES BY RAMAN SPECTROSCOPY

This application claims the benefit of provisional application 60/345,337, filed Nov. 09, 2001.

FIELD OF THE INVENTION

The present invention is directed generally to methods of measuring polymer properties on-line in a polymerization reactor system, and using those measured properties to control the polymerization reaction. In particular, the present invention provides methods of measuring properties of polyolefins such as melt index and density on-line, using Raman spectroscopy, and methods of controlling a reactor using real-time, on-line polymer property data provided by Raman spectroscopic measurements.

BACKGROUND

Gas phase processes for the homopolymerization and copolymerization of monomers, especially olefin monomers, are well known in the art. Such processes can be conducted, for example, by introducing the gaseous monomer or monomers into a stirred and/or fluidized bed of resin particles and catalyst.

In the fluidized-bed polymerization of olefins, the polymerization is conducted in a fluidized-bed reactor, wherein a bed of polymer particles is maintained in a fluidized state by means of an ascending gas stream including gaseous reaction monomer. The polymerization of olefins in a stirred-bed reactor differs from polymerization in a gas fluidized-bed reactor by the action of a mechanical stirrer within the reaction zone, which contributes to fluidization of the bed. As used herein, the term "fluidized-bed" also includes stirred-bed processes and reactors.

The start-up of a fluidized bed reactor generally uses a bed of pre-formed polymer particles. During the course of polymerization, fresh polymer is generated by the catalytic polymerization of the monomer, and polymer product is withdrawn to maintain the bed at constant volume. An industrially favored process employs a fluidization grid to distribute the fluidizing gas to the bed, and also to act as a support for the bed when the supply of gas is cut off. The polymer produced is generally withdrawn from the reactor via one or more discharge conduits disposed in the lower portion of the reactor, near the fluidization grid. The fluidized bed includes a bed of growing polymer particles, polymer product particles and catalyst particles. This reaction mixture is maintained in a fluidized condition by the continuous upward flow from the base of the reactor of a fluidizing gas which includes recycle gas drawn from the top of the reactor, together with added make-up monomer.

The fluidizing gas enters the bottom of the reactor and is passed, preferably through a fluidization grid, upwardly through the fluidized bed.

The polymerization of olefins is an exothermic reaction, and it is therefore necessary to cool the bed to remove the heat of polymerization. In the absence of such cooling, the bed would increase in temperature until, for example, the catalyst became inactive or the polymer particles melted and began to fuse.

In the fluidized-bed polymerization of olefins, a typical method for removing the heat of polymerization is by passing a cooling gas, such as the fluidizing gas, which is at a temperature lower than the desired polymerization temperature, through the fluidized-bed to conduct away the heat of polymerization. The gas is removed from the reactor, cooled by passage through an external heat exchanger and then recycled to the bed.

The temperature of the recycle gas can be adjusted in the heat exchanger to maintain the fluidized-bed at the desired polymerization temperature. In this method of polymerizing alpha olefins, the recycle gas generally includes one or more monomeric olefins, optionally together with, for example, an inert diluent gas or a gaseous chain transfer agent such as hydrogen. The recycle gas thus serves to supply monomer to the bed to fluidize the bed and to maintain the bed within a desired temperature range. Monomers consumed by conversion into polymer in the course of the polymerization reaction are normally replaced by adding make-up monomer to the recycle gas stream.

The material exiting the reactor includes the polyolefin and a recycle stream containing unreacted monomer gases. Following polymerization, the polymer is recovered. If desired, the recycle stream can be compressed and cooled, and mixed with feed components, whereupon a gas phase and a liquid phase are then returned to the reactor.

The polymerization process can use Ziegler-Natta and/or metallocene catalysts. A variety of gas phase polymerization processes are known. For example, the recycle stream can be cooled to a temperature below the dew point, resulting in condensing a portion of the recycle stream, as described in U.S. Pat. Nos. 4,543,399 and 4,588,790. This intentional introduction of a liquid into a recycle stream or reactor during the process is referred to generally as a "condensed mode" operation.

Further details of fluidized bed reactors and their operation are disclosed in, for example, U.S. Pat. Nos. 4,243,619, 4,543,399, 5,352,749, 5,436,304, 5,405,922, 5,462,999, and 6,218,484, the disclosures of which are incorporated herein by reference.

The properties of the polymer produced in the reactor are affected by a variety of operating parameters, such as temperatures, monomer feed rates, catalyst feed rates, and hydrogen gas concentration. In order to produce polymer having a desired set of properties, such as melt index and density, polymer exiting the reactor is sampled and laboratory measurements carried out to characterize the polymer. If it is discovered that one or more polymer properties are outside a desired range, polymerization conditions can be adjusted, and the polymer resampled. This periodic sampling, testing and adjusting, however, is undesirably slow, since sampling and laboratory testing of polymer properties such as melt index, molecular weight distribution and density is time-consuming. As a result, conventional processes can produce large quantities of "off-spec" polymer before manual testing and control can effectively adjust the polymerization conditions. This occurs during production of a particular grade of resin as well as during the transition process between grades.

Methods have been developed to attempt to provide rapid assessment of certain polymer properties and rapid adjustment of polymerization conditions. PCT publications WO 01/09201 and WO 01/09203 disclose Raman-based methods using principal components analysis (PCA) and partial least squares (PLS) to determine concentrations of components in a slurry reactor. The concentration of a particular component, such as ethylene or hexene, is determined based on measurements of a known Raman peak corresponding to the component. U.S. Pat. No. 5,999,255 discloses a method for measuring a physical property of a polymer sample, preferably nylon, by measuring a portion of a Raman spectrum of the polymer sample, determining a value of a preselected spectral feature from the Raman spectrum, and comparing the determined value to reference values. This method relies on identification and monitoring of preselected spectral features corresponding to identified functional groups, such as NH or methyl, of the polymer.

Additional background information can be found in U.S. Pat. Nos. 6,144,897 and 5,151,474; European Patent application EP 0 561 078; PCT publication WO 98/08066; and Ardell, G. G. et al., "Model Prediction for Reactor Control," *Chemical Engineering Progress*, American Institute of Chemical Engineers, U.S., vol. 79, no. 6, Jun. 1, 1983, pages 77–83 (ISSN 0360-7275).

It would be desirable to have methods of determining polymer properties such as melt index, density and molecular weight distribution, on-line in a fluidized bed polymerization reactor, without the need to preselect or identify spectral features of a polymer to monitor. It would also be desirable to have methods of controlling a gas-phase fluidized bed reactor to maintain desired polymer properties, based on a rapid, on-line determination of the polymer properties.

SUMMARY OF THE INVENTION

In one aspect, the present invention provides a process for determining polymer properties in a polymerization reactor system. The process includes obtaining a regression model for determining a polymer property, the regression model including principal component loadings and principal component scores, acquiring a Raman spectrum of a polyolefin sample comprising polyolefin, calculating a new principal component score from at least a portion of the Raman spectrum and the principal component loadings, and calculating the polymer property by applying the new principal component score to the regression model.

In another aspect, the present invention provides a process for controlling polymer properties in a polymerization reactor system. The process includes obtaining a regression model for determining a polymer property, the regression model including principal component loadings and principal component scores, acquiring a Raman spectrum of a polyolefin sample comprising polyolefin, calculating a new principal component score from at least a portion of the Raman spectrum and the principal component loadings, calculating the polymer property by applying the new principal component score to the regression model, and adjusting at least one polymerization parameter based on the calculated polymer property. In particular embodiments, the at least one polymerization parameter can be, for example, monomer feed rate, comonomer feed rate, catalyst feed rate, hydrogen gas feed rate, or reaction temperature.

In one embodiment, the regression model is constructed by obtaining a plurality of Raman spectra of polyolefin samples, calculating principal component loadings and principal component scores from the spectra using principal component analysis (PCA), and forming the regression model using the principal component scores such that the regression model correlates the polymer property to the principal component scores.

In another embodiment, the regression model is a locally weighted regression model.

In another embodiment, the method includes: obtaining a first regression model for determining a first polymer property, the first regression model including first principal component loadings and first principal component scores; obtaining a second regression model for determining a second polymer property, the second regression model including second principal component loadings and second principal component scores; acquiring a Raman spectrum of a sample comprising polyolefin; calculating a new first principal component score from at least a portion of the Raman spectrum and the first principal component loadings; calculating a new second principal component score from at least a portion of the Raman spectrum and the second principal component loadings; calculating the first polymer property by applying the new first principal component score to the first regression model; and calculating the second polymer property by applying the new second principal component score to the second regression model.

In another embodiment, the sample includes polyolefin particles.

In another embodiment, the Raman spectrum is acquired by providing a sample of polyolefin particles and irradiating the sample and collecting scattered radiation during a sampling interval using a sampling probe, wherein there is relative motion between the sample and the sampling probe during at least a portion of the sampling interval. The relative motion serves to effectively increase the field of view of the sampling probe, providing more accurate data.

In another embodiment, the polymerization reactor is a fluidized-bed reactor.

In other embodiments, suitable polymer properties include, for example, density, melt flow rates such as melt index or flow index, molecular weight, molecular weight distribution, and various functions of such properties.

DETAILED DESCRIPTION

In one embodiment, the present invention provides a method of determining polyolefin polymer properties on-line, i.e., as the polyolefin is produced in a reactor system, without the need for external sampling and analysis. The method includes obtaining a regression model for determining a polymer property, the regression model including principal component loadings and principal component scores, acquiring a Raman spectrum of a polyolefin sample, calculating a new principal component score from at least a portion of the Raman spectrum and the principal component loadings, and calculating the polymer property by applying the new principal component score to the regression model.

In one embodiment, the method is used to determine polymer properties on-line in a fluidized-bed reactor system. Fluidized-bed reactors are well-known in the art; a particular, non-limiting example of a fluidized bed reactor is described herein, for illustrative purposes only. Those skilled in the art will recognize that numerous modifications and enhancements can be made, as desired, to the fluidized-bed reactor.

Fluidized-Bed Reactor

Figure 1:
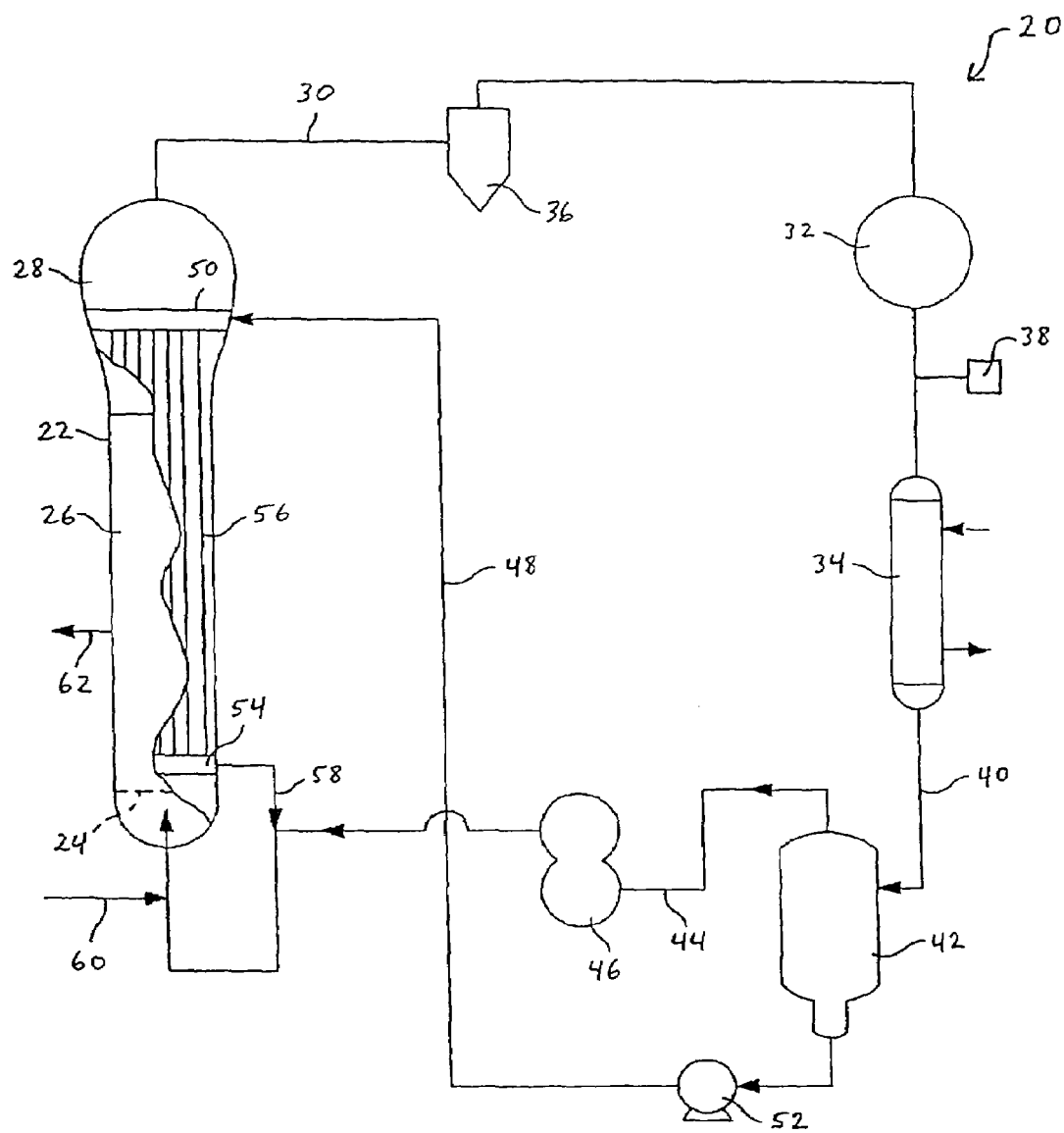
FIG. 1 is a block diagram of a gas-phase reactor.

FIG. 1 illustrates a gas-phase fluidized bed reactor 20 having a reactor body 22, which is generally an upright cylinder having a fluidization grid 24 located in its lower regions. The reactor body 22 encloses a fluidized bed zone 26 and a velocity reduction zone 28 which is generally of increased diameter compared to the diameter of the fluidized bed zone 26 of the reactor body 22.

The gaseous reaction mixture leaving the top of the reactor body 22, the "recycle gas stream," contains principally unreacted monomer, unreacted hydrogen gas, inert condensable gases such as isopentane, and inert non-condensable gases such as nitrogen. The recycle gas stream is transferred via line 30 to compressor 32, and from compressor 32 to heat exchanger 34. An optional cyclone separator 36 may be used as shown, preferably upstream of compressor 32, to remove fines, if desired. An optional gas analyzer 38 can be used if desired, to sample the recycle gas stream to determine concentrations of various components. Typically, the gas analyzer is a gas phase chromatograph (GPC), or a spectrograph such as a near-infrared spectrometer or a fourier transform near-infrared spectrometer (FT-NIR). An additional heat exchanger (not shown) may also be used if desired, preferably upstream of compressor 32.

The cooled recycle gas stream exits the heat exchanger 34 via line 40. As discussed above, the cooled recycle gas stream can be gaseous, or can be a mixture of gaseous and liquid phases. FIG. 1 shows an optional configuration wherein at least a portion of the recycle gas stream is cooled to a temperature at or below the temperature where liquid condensate begins to form (the dew point). All or a portion of the resultant gas liquid mixture is transferred via line 40 to a separator 42, where all or a portion of the liquid is removed. All or a portion of the gas stream, which may contain some liquid, is transferred via line 44 to a point below the fluidization grid 24 in the lower region of the reactor. An amount of upwardly flowing gas, sufficient to maintain the bed in a fluidized condition, is provided in this way.

Those skilled in the art will understand that less gas is required to maintain fluidization when the reactor employed is a stirred bed reactor.

An optional compressor 46 may be provided to ensure that a sufficient velocity is imparted to the gases flowing through line 44 into the bottom of the reactor. The gas stream entering the bottom of the reactor may contain condensed liquid, if desired.

All or a portion of the liquid phase separated from the recycle stream in separator 42 is transferred via line 48 to a manifold 50 located at or near the top of the reactor. If desired, a pump 52 may be provided in line 48 to facilitate the transfer of liquid to manifold 50. The liquid entering manifold 50 flows downward into manifold 54 through a plurality of conduits 56 which have good heat exchange properties and which are in heat exchange contact with the wall of the reactor. The passage of liquid through the conduits 56 cools the interior wall of the reactor and warms the liquid to a greater or lesser extent, depending upon the temperature differential and the duration and extent of heat exchange contact. Thus by the time the liquid entering manifold 50 reaches manifold 54, it has become a heated fluid which may have remained in an entirely liquid state or it may have become partially or totally vaporized.

As shown in FIG. 1, the heated fluid (gas and/or liquid) is passed from manifold 54 via line 58 to combine with gases leaving the separator 42 via line 44, prior to entry into the reactor in the region below the fluidization grid 24. In like manner, make-up monomer can be introduced into the reactor in either liquid or gaseous form via line 60. Gas and/or liquid collected in manifold 54 may also be transferred directly into the reactor (not shown) in the region below the fluidization grid.

Product polymer particles can be removed from the reactor via line 62 in the conventional way, as for example by the method and apparatus described in U.S. Pat. No. 4,621,952. Although only one line 62 is shown in the Figure, typical reactors can include more than one line 62.

Catalyst is continuously or intermittently injected into the reactor using a catalyst feeder (not shown) such as the device disclosed in U.S. Pat. No. 3,779,712. The catalyst is preferably fed into the reactor at a point 20 to 40 percent of the reactor diameter away from the reactor wall and at a height of about 5 to about 30 percent of the height of the bed. The catalyst can be any catalyst suitable for use in a fluidized bed reactor and capable of polymerizing ethylene, such as one or more metallocene catalysts, one or more Ziegler-Natta catalysts, bimetallilic catalysts, or mixtures of catalysts.

A gas which is inert to the catalyst, such as nitrogen or argon, is preferably used to carry catalyst into the bed. Cold condensed liquid from either separator 42 or from manifold 54 may also be used to transport catalyst into the bed.

In methods of the present invention, the fluidized bed reactor is operated to form at least one polyolefin homopolymer or copolymer. Suitable polyolefins include, but are not limited to, polyethylene, polypropylene, polyisobutylene, and homopolymers and copolymers thereof.

In one embodiment, the at least one polyolefin includes polyethylene homopolymer and/or copolymer. Low density polyethylene ("LDPE") can be prepared at high pressure using free radical initiators, or in gas phase processes using Ziegler-Natta or vanadium catalysts, and typically has a density in the range of 0.916–0.940 g/cm$^3$. LDPE is also known as "branched" or "heterogeneously branched" polyethylene because of the relatively large number of long chain branches extending from the main polymer backbone. Polyethylene in the same density range, i.e., 0.916 to 0.940 g/cm$^3$, which is linear and does not contain long chain branching is also known; this "linear low density polyethylene" ("LLDPE") can be produced with conventional Ziegler-Natta catalysts or with metallocene catalysts. Relatively higher density LDPE, typically in the range of 0.928 to 0.940 g/cm$^3$, is sometimes referred to as medium density polyethylene ("MDPE"). Polyethylenes having still greater density are the high density polyethylenes ("HDPEs"), i.e., polyethylenes having densities greater than 0.940 g/cm$^3$, and are generally prepared with Ziegler-Natta catalysts. Very low density polyethylene ("VLDPE") is also known. VLDPEs can be produced by a number of different processes yielding polymers with different properties, but can be generally described as polyethylenes having a density less than 0.916 g/cm$^3$, typically 0.890 to 0.915 g/cm$^3$ or 0.900 to 0.915 g/cm$^3$.

Polymers having more than two types of monomers, such as terpolymers, are also included within the term "copolymer" as used herein. Suitable comonomers include α-olefins, such as $C_3$–$C_{20}$ α-olefins or $C_3$–$C_{12}$ α-olefins. The α-olefin comonomer can be linear or branched, and two or more comonomers can be used, if desired. Examples of suitable comonomers include linear $C_3$–$C_{12}$ α-olefins, and α-olefins having one or more $C_1$–$C_3$ alkyl branches, or an aryl group. Specific examples include propylene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. It should be appreciated that the list of comonomers above is merely exemplary, and is not intended to be limiting. Preferred comonomers include propylene, 1-butene, 1-pentene, 4-methyl-1-pentene, 1-hexene, 1-octene and styrene.

Other useful comonomers include polar vinyl, conjugated and non-conjugated dienes, acetylene and aldehyde monomers, which can be included in minor amounts in terpolymer compositions. Non-conjugated dienes useful as comonomers preferably are straight chain, hydrocarbon diolefins or cycloalkenyl-substituted alkenes, having 6 to 15 carbon atoms. Suitable non-conjugated dienes include, for example: (a) straight chain acyclic dienes, such as 1,4-hexadiene and 1,6-octadiene; (b) branched chain acyclic dienes, such as 5-methyl-1,4-hexadiene; 3,7-dimethyl-1,6-octadiene; and 3,7-dimethyl-1,7-octadiene; (c) single ring alicyclic dienes, such as 1,4-cyclohexadiene; 1,5-cyclo-octadiene and 1,7-cyclododecadiene; (d) multi-ring alicyclic fused and bridged ring dienes, such as tetrahydroindene; norbornadiene; methyl-tetrahydroindene; dicyclopentadiene (DCPD); bicyclo-(2.2.1)-hepta-2,5-diene; alkenyl, alkylidene, cycloalkenyl and cycloalkylidene norbornenes, such as 5-methylene-2-norbornene (MNB), 5-propenyl-2-norbornene, 5-isopropylidene-2-norbornene, 5-(4-cyclopentenyl)-2-norbornene, 5-cyclohexylidene-2-norbornene, and 5-vinyl-2-norbornene (VNB); and (e) cycloalkenyl-substituted alkenes, such as vinyl cyclohexene, allyl cyclohexene, vinyl cyclooctene, 4-vinyl cyclohexene, allyl cyclodecene, and vinyl cyclododecene. Of the non-conjugated dienes typically used, the preferred dienes are dicyclopentadiene, 1,4-hexadiene, 5-methylene-2-norbornene, 5-ethylidene-2-norbornene, and tetracyclo-(Δ-11,12)-5,8-dodecene. Particularly preferred diolefins are 5-ethylidene-2-norbornene (ENB), 1,4-hexadiene, dicyclopentadiene (DCPD), norbornadiene, and 5-vinyl-2-norbornene (VNB).

The amount of comonomer used will depend upon the desired density of the polyolefin and the specific comonomers selected. One skilled in the art can readily determine the appropriate comonomer content appropriate to produce a polyolefin having a desired density.

Raman Spectroscopy

Raman spectroscopy is a well-known analytical tool for molecular characterization, identification, and quantification. Raman spectroscopy makes use of inelastically scattered radiation from a non-resonant, non-ionizing radiation source, typically a visible or near-infrared radiation source, such as a laser, to obtain information about molecular vibrational-rotational states. In general, non-ionizing, non-resonant radiation is scattered elastically and isotropically (Raleigh scattering) from a scattering center, such as a molecule. Subject to well-known symmetry and selection rules, a very small fraction of the incident radiation can be inelastically and isotropically scattered, with each inelastically scattered photon having an energy $E = h\upsilon_0 \pm |E_{i',j'} - E_{i,j}|$, where $h\upsilon_0$ is the energy of the incident photon and $|E_{i',j'} - E_{i,j}|$ is the absolute difference in energy between the final (i',j') and initial (i,j) vibrational-rotational states of the molecule. This inelastically scattered radiation is the Raman scattering, and includes both Stokes scattering, where the scattered photon has lower energy than the incident photon ($E = h\upsilon_0 - |E_{i',j'} - E_{i,j}|$), and anti-Stokes scattering, where the scattered photon has higher energy than the incident photon ($E = h\upsilon_0 + |E_{i',j'} - E_{i,j}|$).

Raman spectra are typically shown as plots of intensity (arbitrary units) versus "Raman shift", where the Raman shift is the difference in energy or wavelength between the excitation radiation and the scattered radiation. The Raman shift is typically reported in units of wavenumbers (cm$^{-1}$), i.e., the reciprocal of the wavelength shift in centimeters. Energy difference $|E_{i',j'} - E_{i,j}|$ and wavenumbers (ω) are related by the expression $|E_{i',j'} - E_{i,j}| = hc\omega$, where h is Planck's constant, c is the speed of light in cm/s, and ω is the reciprocal of the wavelength shift in centimeters.

The spectral range of the Raman spectrum acquired is not particularly limited, but a useful range includes Raman shifts (Stokes and/or anti-Stokes) corresponding to a typical range of polyatomic vibrational frequencies, generally from about 100 cm$^{-1}$ to about 4000 cm$^{-1}$. It should be appreciated that useful spectral information is present in lower and higher frequency regions. For example, numerous low frequency molecular modes contribute to Raman scattering in the region below 100 cm$^{-1}$ Raman shift, and overtone vibrations (harmonics) contribute to Raman scattering in the region above 4000 cm$^{-1}$ Raman shift. Thus, if desired, acquisition and use of a Raman spectrum as described herein can include these lower and higher frequency spectral regions.

Conversely, the spectral region acquired can be less than all of the 100 cm$^{-1}$ to 4000 cm$^{-1}$ region. For many polyolefins, the majority of Raman scattering intensity will be present in a region from about 500 cm$^{-1}$ to about 3500 cm$^{-1}$ or from 1000 cm$^{-1}$ to 3000 cm$^{-1}$. The region acquired can also include a plurality of sub-regions that need not be contiguous.

As explained below, it is a particular advantage of the methods described herein that Raman scattering intensity data is useful in determining properties of polyolefin particles without the need to identify, select, or resolve particular spectral features. Thus, it is not necessary to identify a particular spectral feature as being due to a particular mode of a particular moiety of the polyolefin, nor is it necessary to selectively monitor Raman scattering corresponding to a selected spectral feature. Indeed, it has been surprisingly found that such selective monitoring disadvantageously disregards a wealth of information content embedded in the spectrum that, heretofore, has generally been considered to be merely unusable scattering intensity disposed between and underlying the identifiable (and thus presumed useful) bands. Accordingly, in the methods described herein, the Raman spectral data acquired and used includes a plurality of frequency or wavelength shift, scattering intensity (x, y) measurements over relatively broad spectral regions, including regions conventionally identified as spectral bands and regions conventionally identified as interband, or unresolved regions.

The frequency spacing of acquired data can be readily determined by one skilled in the art, based on considerations of machine resolution and capacity, acquisition time, data analysis time, and information density. Similarly, the amount of signal averaging used is readily determined by one skilled in the art based on machine and process efficiencies and limitations.

The spectral region measured can include Stokes scattering (i.e., radiation scattered at frequencies lower than the excitation frequency), anti-Stokes scattering (i.e., radiation scattered at frequencies higher than the excitation frequency), or both. Optionally, polarization information embedded in the Raman scattering signal can also be used, and one skilled in the art readily understands how to acquire Raman polarization information. However, determining polymer properties as described herein does not require the use of polarization information. In some embodiments described herein, any Raman polarization is essentially randomized as a result of interactions with the fiber optic conduit used to convey the signal to the signal analyzer, as described below.

Raman Instrumentation

Figure 2:
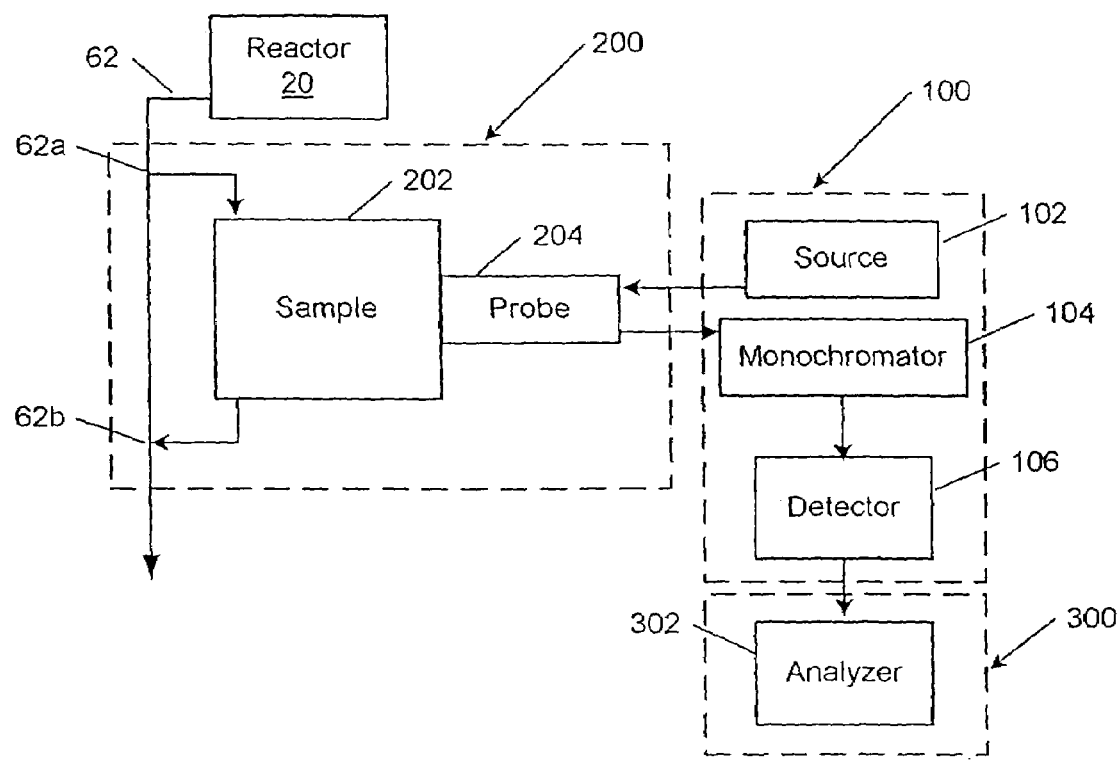
FIG. 2 is a block diagram of a Raman analyzer according to the invention.

Referring now to FIG. 2, the instrumentation used to collect and process Raman data includes a Raman subsystem 100, a sample subsystem 200, and a data subsystem 300. As shown in FIG. 2, the sample subsystem 200 is in communication with reactor 20 via polymer output line 62 (see also FIG. 1). Each of these subsystems is described below.

Raman Subsystem

The Raman subsystem includes a Raman spectrometer, the principal components of which are an excitation source 102, a monochromator 104, and a detector 106. Raman spectrometers are well-known analytical instruments, and thus only a brief description is provided herein.

A Raman spectrometer includes an excitation source 102 which delivers excitation radiation to the sample subsystem 200. Scattered radiation is collected within the sample subsystem 200 (described below), filtered of Raleigh scattered light, and dispersed via monochromator 104. The dispersed Raman scattered light is then imaged onto a detector 106 and subsequently processed in data subsystem 300, as further described below.

Excitation Source

The excitation source and frequency can be readily determined based on considerations well-known in the art. Typically, the excitation source 102 is a visible or near infrared laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used. It is well-known that scattering, including Raman scattering, is proportional to the fourth power of the excitation frequency, subject to the practical limitation that fluorescence typically overwhelms the relatively weak Raman signal at higher frequencies. Thus, higher frequency (shorter wavelength) sources are preferred to maximize signal, while lower frequency (longer wavelength) sources are preferred to minimize fluorescence. One skilled in the art can readily determine the appropriate excitation source based on these and other considerations, such as mode stability, maintenance time and costs, capital costs, and other factors well understood in the art.

The excitation radiation can be delivered to the sample subsystem 200, and the scattered radiation collected from the sample subsystem, by any convenient means known in the art, such as conventional beam manipulation optics, or fiber optic cables. For an on-line process measurement, it is particularly convenient to deliver the excitation radiation and collect the scattered radiation fiber-optically. It is a particular advantage of Raman spectroscopy that the excitation radiation typically used is readily manipulated fiber optically, and thus the excitation source can be positioned remotely from the sampling region. A particular fiber optic probe is described below; however, one skilled in the art will appreciate that the Raman system is not limited to any particular means of radiation manipulation.

Monochromator

The scattered radiation is collected and dispersed by any convenient means known in the art, such as a fiber optic probe as described below. The collected scattered radiation is filtered to remove Raleigh scattering and optionally filtered to remove fluorescence, then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator 104 can be any such dispersive element, along with associated filters and beam manipulation optics.

Detector

The dispersed Raman scattering is imaged onto a detector 106. The choice of detector is easily made by one skilled in the art, taking into account various factors such as resolution, sensitivity to the appropriate frequency range, response time, etc. Typical detectors include array detectors generally used with fixed-dispersive monochromators, such as diode arrays or charge coupled devices (CCDs), or single element detectors generally used with scanning-dispersive monochromators, such as lead sulfide detectors and indium-gallium-arsenide detectors. In the case of array detectors, the detector is calibrated such that the frequency (wavelength) corresponding to each detector element is known. The detector response is delivered to the data subsystem 300 which generates a set of frequency shift, intensity (x,y) data points which constitute the Raman spectrum.

Sample Subsystem

The sample subsystem 200 couples the Raman subsystem 100 to the polymerization process. Thus, the sample subsystem 200 delivers the excitation radiation from the excitation source 102 to the polymer sample, collects the scattered radiation, and delivers the scattered radiation to the monochromator 104.

As noted above, the excitation radiation can be delivered to and collected from the polymer sample by any convenient means, such as using conventional optics or fiber optic cables.

Figure 3:
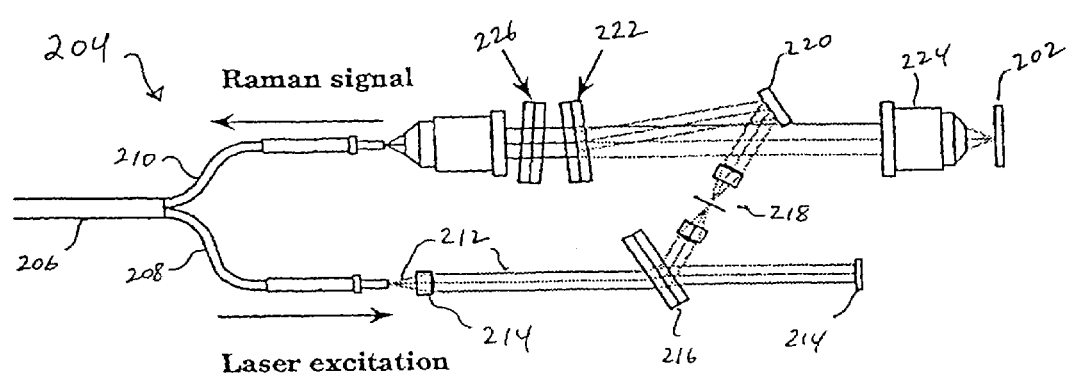
FIG. 3 illustrates one embodiment of a fiber optic Raman probe.

In one embodiment, the sample subsystem includes a probe 204 and a sample chamber 202. FIG. 3 shows a block diagram of one embodiment of a fiber optic probe. The probe includes a fiber optic bundle 206 including one or more fiber optic cables 208 carrying the excitation radiation from the excitation source toward the sample, and one or more fiber optic cables 210 carrying the collected scattered radiation from the sample. Fiber optic cables 208 are in optical communication with the excitation source (102 in FIG. 2), and fiber optic cables 210 are in optical communication with the monochromator (104 in FIG. 2). The excitation and scattered radiation can be manipulated using well-known techniques. Thus, it should be appreciated that the particular optical setup shown in FIG. 3 is merely exemplary. Excitation radiation 212 is directed via optics 214 to a holographic grating 216 and spatial filter 218 to remove silica Raman due to the fiber optic cable, then directed via mirror 220 and beam combiner 222 to sampling optics 224 and sample chamber 202. Scattered radiation is collected via sampling optics 224 and directed through beam combiner 222, a notch filter 226 to remove the Raleigh scattered radiation, and into fiber optic cables 210.

The sample in the sample chamber includes a plurality of polymer particles (granules), and represents the polymer product as discharged from the reactor. Advantageously, it is not necessary that the sample be free of liquid-phase components, such as residual solvent or other liquid hydrocarbons that may be present in the polymer in the discharge line of a fluidized-bed reactor.

Raman probes such as described herein are imaging, in that they have a focused field of view. An imaging probe is the most efficient optical configuration, and because the Raman signal is weak the imaging probe collects as much scattered light as possible. A disadvantage of an imaging probe is that the probe "sees" only a very small amount of the sample at any one time. For a typical fluidized-bed process, a fixed imaging probe has a field of view corresponding to only 1 or 2 polymer granules. Thus, the data collected in a static mode may not be representative of the bulk material.

In one embodiment, the disadvantage of a limited field of view is overcome by providing relative motion between the sample and the Raman probe, so that the probe collects scattering from many polymer granules over the course of the sampling interval. Thus, for example, the probe can be moved through the sample during at least a portion of the sampling interval or, equivalently, the sample or sample chamber can be moved relative to a fixed probe during at least a portion of the sampling interval, or both can be moved. In a particular embodiment, it is convenient to keep the sample chamber stationary and move the Raman probe into and out of the sample chamber during the sampling interval by linearly translating the probe using a linear actuator. One skilled in the art will readily appreciate, however, that relative motion between the sample granules and the probe can be achieved by numerous other mechanisms, such as, for example, allowing polymer granules to pass by a stationary probe.

As a specific example, a particular sampling system used in Examples 4–7 below is now described. It should be appreciated that this particular system is exemplary and not limiting.

Figure 4:
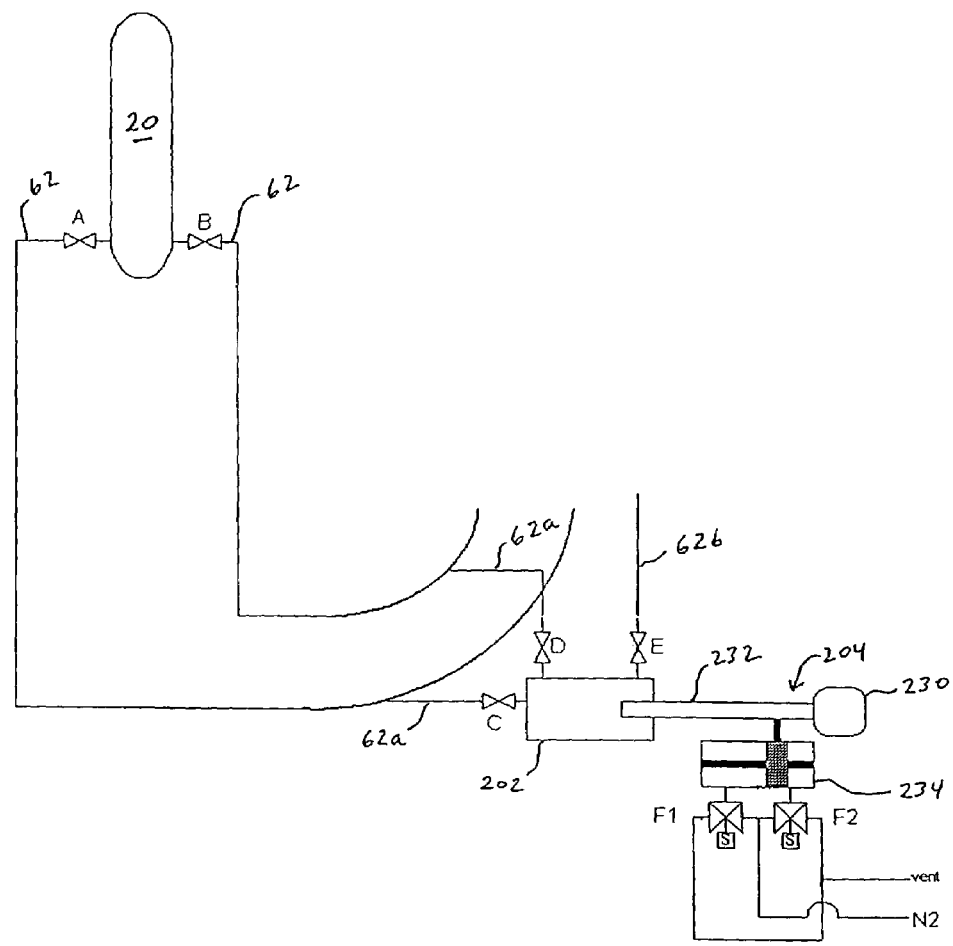
FIG. 4 illustrates one embodiment of a sample chamber.
Figure 5:
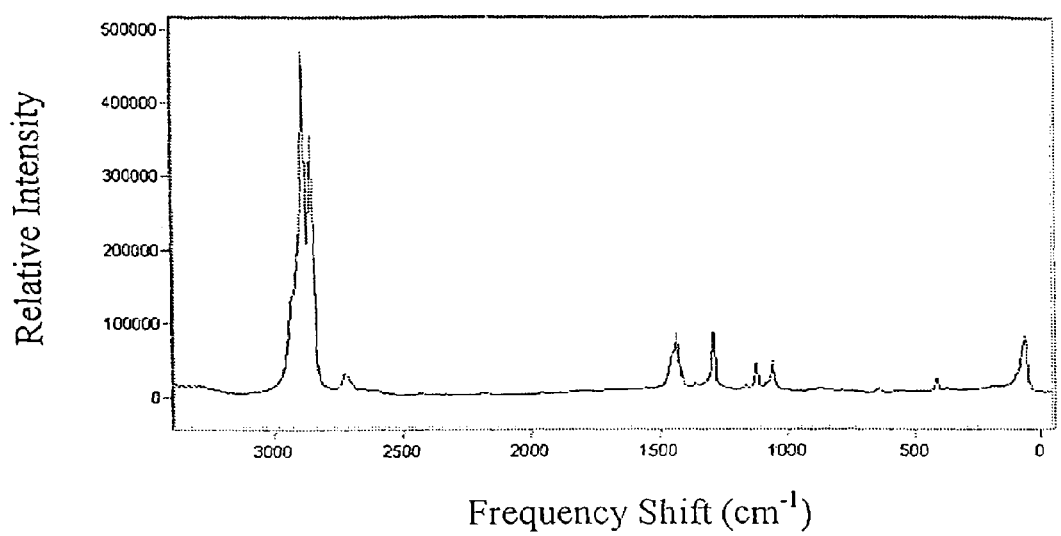
FIG. 5 is a representative Raman spectrum of a granular linear low polyethylene polymer sample.

A fluidized-bed polymerization plant having two reactors was used, with one reactor producing metallocene-catalyzed LLDPE resin, and the other reactor producing Ziegler-Natta catalyzed LLDPE resin. Referring now to FIG. 4, each reactor 20 (only one reactor shown) has two dump valves A and B that alternate to remove product from the reactor. The product is pneumatically conveyed through product discharge pipe 62 with 90 psi (0.6 MPa) nitrogen at a speed of about 60 miles per hour (0.4 m/s). At this speed the slug of product dumped from a reactor will only be present at any one point in the pipe for a few seconds. However, it is preferred to average the Raman signal for 60–120 seconds to improve the signal-to-noise ratio. To accomplish this, a small amount of product (about 800 grams) is trapped and held in a sample chamber 202 as the slug passes through the product discharge pipe 62. The sample chamber 202 is attached to the product discharge pipe 62 by a 1 inch (25 mm) diameter pipe 62b and a pneumatically actuated valve C or D. The operation of the valves C and D is controlled by the Raman analyzer, but could also be controlled by an auxiliary system. The Raman analyzer waits for a signal from the reactor telling it that the dump valve A or B has opened. The Raman analyzer then opens valve C or D connecting the sample chamber 202 to the product discharge pipe 62, and waits for a time predetermined to be sufficient to have allowed the slug of product to have passed by the sample capture point. The Raman analyzer next closes the sample capture valve C or D, trapping the captured sample of product in the sample chamber 202.

The Raman analyzer probe 204 includes a probe head 230 enclosing the filtering and optical (not electronic) signal processing elements, and a sample interface 232, which is an 8" long by 0.5" diameter (20 cm×1.3 cm) tube. Tube 232 is inserted through the end of the sample chamber opposite to where the sample enters, so that it comes in contact with the sample. A pneumatic linear actuator 234 is attached to the probe 204 to slowly draw the probe out of the sample chamber and then reinsert it during a sample collection interval. This probe movement causes sample to flow across the front of the probe, providing a continually changing sample for measurement.

The reactor 20 dumps on a 3–6 minute cycle (grade dependent), alternating between 2 lines 62 controlled by valves A and B. Sample is collected from only one of the lines. The sample system operates by waiting for a Sample Ready signal from the reactor telling the Raman analyzer that a sample is being dumped. The Sample Ready signal is in the form of a digital input to the Raman analyzer. When the analyzer receives the Sample Ready signal, there is a sequence of tasks it performs prior to setting up the valves for the Capture Sample operation, which are:

Check to determine if the Sample Ready is for the next stream. In the Raman control software, there is a stream sequence list that the operator sets to tell the analyzer which reactor(s) to sample and measure. Typically, this would be 1,2,1,2, etc., for a two reactor system, but under some circumstances such as a grade transition on reactor 1, the operator might want to sample, for example, 1,1,1,2,1,1,1,2, etc. Thus, the analyzer checks to make sure the dump indicator it receives is consistent with the current stream sequence. If not, the analyzer ignores the signal.

Check that the Reactor On-line digital input for this reactor is valid. The typical stream sequence 1,2,1,2 . . . may be in effect, but the operator may decide to only monitor a single reactor, such as during a transition or upset. The reactor receives separate digital inputs for each reactor, which tell it whether or not to sample a particular reactor regardless of the active or current stream sequence list.

Wait a set time interval between the Sample Ready signal and setting valves for Capture Sample.

Set Valves for Capture Sample.

The valve states are shown in the table below for a sequence sampling through the A valve of product discharge line 62, with state "C" being closed, and state "O" being open.

Valve States For Sampling

| | Valve | | | | | |
|---|---|---|---|---|---|---|
| | A | B | C | D | E | F |
| Waiting for Sample | C | C | C | C | C | C |
| Capture Sample | O | C | O | O | C | C |
| Measure Spectrum | C | C | C | C | C | O |
| Eject Sample | C | C | O | C | O | O |
| Reset Probe | C | C | O | C | O | C |

Sample Capture is accomplished by opening the sample chamber valves C and D. In the configuration where product is discharged through the A valve of product discharge line 62, an open valve C permits the sample to enter sample chamber 202, and an open valve D serves as a vent. A portion of the discharged polymer product in 90 psig nitrogen being transported at about 60 miles per hour packs into the sample chamber 202 attached to a bend in the product discharge line 62. Once the sample chamber 202 is full, the analyzer performs a series of operations to complete data collection and prepare for the next sample. These operations include:

Wait a specified time interval after the Capture Sample valve state is set.
Set the Measure Spectrum valve state.
Eject the sample
Reset the Probe Position.
Set the Waiting for Sample valve state
Update the stream sequence information.

The probe is attached to linear actuator so that it can be moved in and out of the sample chamber. In the Waiting for Sample state (5), the probe is fully inserted into the sample chamber so that the shaft of the probe is immersed in sample after the chamber is filled. The Measure Spectrum valve state (2) not only closes valves C and D, but also actuates both three-way valves controlling the linear actuator so that the probe is slowly extracted from the sample chamber while data is being collected. Upon completion of the Spectrum Collect operation, the sample in the sample chamber is ejected back into the sample transport line by opening valves C and E.

Data Subsystem

Referring again to FIG. 2, the data subsystem includes an analyzer 302, which receives the response signal of the detector 106. The analyzer can be, for example, a computer capable of storing and processing the Raman data. Other functions of the analyzer can include, for example, developing the regression model and carrying out PCA/LWR analysis, as described below. In one embodiment described above, the data subsystem controls the motion of the sampling probe. In another embodiment described above, the data subsystem controls valves for filling and emptying the sample chamber. In another embodiment, the data subsystem compares the calculated value of one or more polymer properties to a target value, and adjusts one or more reactor parameters in response to the deviation between calculated and target values. Reactor control is further described below.

PCA/LWR Analysis

The Raman spectrum includes information directly or indirectly related to various properties of the polyolefin sample. Conventionally, sample components are identified by the presence of unique spectral signatures, such as particular bands recognized as being due to particular vibrational modes of a molecule. Quantitative information such as concentration can then be obtained about a sample component by, for example, integrating the area under a particular peak and comparing the area to a calibration sample, by monitoring scattered intensity at a particular peak as a function of time, etc. In contrast to these conventional approaches, the present inventors have surprisingly found that polymer properties can be determined from Raman spectra without the need to identify or select particular spectral features, by using a multivariate model to correlate polymer properties with Raman scattering data. The model uses large, contiguous regions of the spectrum, rather than discrete spectral bands, thereby capturing large amounts of information density unavailable and unrecognized in conventional analysis. Further, the spectral data are correlated to polymer properties such as melt flow rates (defined below), densities, molecular weight distributions, etc., that are not readily apparent from optical spectra.

In one embodiment, the data analysis described below is used to build and apply a predictive model for at least one property of the polyolefin particles selected from melt flow rate, density, molecular weight, molecular weight distribution, and functions thereof.

As used herein, the term "melt flow rate" indicates any of the various quantities defined according to ASTM D-1238, including $I_{2.16}$, the melt flow rate of the polymer measured according to ASTM D-1238, condition E (2.16 kg load, 190° C.), commonly termed the "melt index", and $I_{21.6}$, the melt flow rate of the polymer measured according to ASTM D-1238, condition F (21.6 kg load, 190° C.), commonly termed the "flow index." Other melt flow rates can be specified at different temperatures or different loads. The ratio of two melt flow rates is the "Melt Flow Ratio" or MFR, and is most commonly the ratio of $I_{21.6}/I_{2.16}$. "MFR" can be used generally to indicate a ratio of melt flow rates measured at a higher load (numerator) to a lower load (denominator).

As used herein, "molecular weight" indicates any of the moments of the molecular weight distribution, such as the number average, weight average, or Z-average molecular weights, and "molecular weight distribution" indicates the ratio of two such molecular weights. In general, molecular weights M can be computed from the expression:

$$M = \frac{\sum_i N_i M_i^{n+1}}{\sum_i N_i M_i^n}$$

where $N_i$ is the number of molecules having a molecular weight $M_i$. When n=0, M is the number average molecular weight Mn. When n=1, M is the weight average molecular weight Mw. When n=2, M is the Z-average molecular weight Mz. These and higher moments are included in the term "molecular weight." The desired molecular weight distribution (MWD) function (such as, for example, Mw/Mn or Mz/Mw) is the ratio of the corresponding M values. Measurement of M and MWD by conventional methods such as gel permeation chromatography is well known in the art and is discussed in more detail in, for example, Slade, P. E. Ed., *Polymer Molecular Weights Part II*, Marcel Dekker, Inc., NY, (1975) 287–368; Rodriguez, F., *Principles of Polymer Systems* 3rd ed., Hemisphere Pub. Corp., NY, (1989) 155–160; U.S. Pat. No. 4,540,753; Verstrate et al., *Macromolecules*, vol. 21, (1988) 3360; and references cited therein.

Methods of the invention include obtaining a regression model for determining a polymer property, the regression model including principal component loadings and principal component scores; acquiring a Raman spectrum of a polyolefin sample; calculating a new principal component score from at least a portion of the Raman spectrum and the principal component loadings; and calculating the polymer property by applying the new principal component score to the regression model.

The regression model is preferable a locally weighted regression (LWR) model, using principal component analysis (PCA) eigenvectors. PCA is a well-known analytical method, and is described, for example, in Pirouette™ Multivariate Data Analysis for Windows software manual, Infometrix, Inc, Woodinville, Wash. (1985–2000), PLS_Toolbox™ software manual, Eigenvector Research, Inc., Manson, Wash. (1998), and references cited therein. LWR is described, for example, in Naes and Isaksson, *Analytical Chemistry*, 62, 664–673 (1990), Sekulic et al., *Analytical Chemistry*, 65, 835A–845A (1993), and references cited therein.

Principal Components Analysis is a mathematical method which forms linear combinations of raw variables to construct a set of mutually orthogonal eigenvectors (principal component loadings). Since the eigenvectors are mutually orthogonal, these new variables are uncorrelated. Further, PCA can calculate the eigenvectors in order of decreasing variance. Although the analysis computes a number of eigenvectors equal to the number of original variables, in practice, the first few eigenvectors capture a large amount of the sample variance. Thus, only a relatively small number of eigenvectors is needed to adequately capture the variance, and a large number of eigenvectors capturing minimal variance can be disregarded, if desired.

The data are expressed in an m (row) by n (column) matrix X, with each sample being a row and each variable a column optionally mean centered, autoscaled, scaled by another function or not scaled. The covariance of the data matrix, cov(X), can be expressed as:

$$\mathrm{cov}(X) = X^T X / (m-1)$$

where the superscript T indicates the transpose matrix. The PCA analysis decomposes the data matrix as a linear combination of principal component scores vectors $S_i$ and principal component loading vectors (eigenvectors) $L_i$, as follows:

$$X = S_1 L_1^T + S_2 L_2^T + S_3 L_2^T + \ldots$$

The eigenvectors $L_i$ are eigenvectors of the covariance matrix, with the corresponding eigenvalues $\lambda_i$ indicating the relative amount of covariance captured by each eigenvector. Thus, the linear combination can be truncated after the sum of the remaining eigenvalues reaches an acceptably small value.

A model can be constructed correlating the Raman scattering intensity with a polymer property in PCA space using various linear or nonlinear mathematical models, such as principal components regression (PCR), partial least squares (PLS), projection pursuit regression (PPR), alternating conditional expectations (ACE), multivariate adaptive regression splines (MARS), and neural networks (NN), to name a few.

In a particular embodiment, the model is a locally weighted regression model. Locally Weighted Regression (LWR) assumes that a smooth non-linear function can be approximated by a linear or relatively simple non-linear (such as quadratic) function, with only the closest data points being used in the regression. The q closest points are used and are weighted by proximity, and the regression model is applied to the locally weighted values.

In the calibration phase, Raman spectra are acquired, and the polymer properties of the sample are measured in the laboratory. The properties measured include those that the model will predict, such as density, melt flow rates, molecular weights, molecular weight distributions, and functions thereof. For a desired polymer property, the data set including the measured polymer properties the samples and the Raman spectral data for the samples is decomposed into PCA space to obtain a calibration data set. No particular number of calibration samples is required. One skilled in the art can determine the appropriate number of calibration samples based on the performance of the model and the incremental change in performance with additional calibration data. Similarly, there is no particular number of PCA eigenvectors required, and one skilled in the art can choose an appropriate number based on the amount of variance captured a selected number of eigenvectors and the incremental effect of additional eigenvectors.

The LWR model can be validated using methods known in the art. It is convenient to divide the calibration samples into two sets: a calibration data set, and a validation data set. The calibration data set is used to develop the model, and to predict the appropriate polymer property for the samples in the validation data set, using the validation data set Raman spectra. Since the chosen polymer property for the validation data set samples is both calculated and measured, the effectiveness of the model can be evaluated by comparing the calculated and measured values.

The validated model can then be applied to sample spectra to predict the desired polymer property or properties.

If desired, a single model can be used to predict two or more polymer properties. Preferably, separate models are developed for each polymer property. Thus, in one embodiment, the present invention includes: obtaining a first regression model for determining a first polymer property, the first regression model including first principal component loadings and first principal component scores; obtaining a second regression model for determining a second polymer property, the second regression model including second principal component loadings and second principal component scores; acquiring a Raman spectrum of a sample comprising polyolefin; calculating a new first principal component score from at least a portion of the Raman spectrum and the first principal component loadings; calculating a new second principal component score from at least a portion of the Raman spectrum and the second principal component loadings; calculating the first polymer property by applying the new first principal component score to the first regression model; and calculating the second polymer property by applying the new second principal component score to the second regression model.

Of course, more than two polymer properties can be determined by including third or more regression models. Advantageously, multiple polymer properties can be determined essentially simultaneously by using the same Raman spectrum and applying several regression models to the spectral data.

In a particular embodiment, two regression models are used, and both a melt flow rate (such as melt index $I_{2.16}$ or flow index $I_{21.6}$) and density are determined.

Reaction Control

In one embodiment, the calculated polymer property is compared to a target polymer property, and at least one reactor parameter is adjusted based on the deviation between the calculated and target polymer property. The at least one reactor parameter can include the amounts of monomer, comonomer, catalyst and cocatalyst, the operating temperature of the reactor, the ratio of comonomer(s) to monomer, the ratio of hydrogen to monomer or comonomer, and other parameters that affect the chosen polymer property. For example, if the chosen polymer property is density and the density calculated from the PCA/LWR model is lower than a target density, a reactor parameter can be adjusted to increase density, such as, for example, reducing the comonomer feed rate and/or increasing the monomer feed rate.

For example, in the case of the fluidized bed polymerization of olefins, hydrogen can serve as a chain transfer agent. In this way, the molecular weight of the polymer product can be controlled. Additionally, varying the hydrogen concentration in olefin polymerization reactors can also vary the polymer melt flow rate, such as the melt index $I_{2.16}$ (MI). The present invention allows control of the reactor to produce polymer having a selected MI range. This is accomplished by knowing the relationship between hydrogen concentration and the MI of polymers produced by a specific reactor, and programming the target MI or MI range into a reactor control system processor. By monitoring the polymer MI data generated by the Raman analyzer and comparing this data to the target MI range, the flow of hydrogen into the reactor vessel may be adjusted so that the MI range of the polymer product remains within the target MI range.

It will be understood by those skilled in the art that other reactor constituent properties and other reactor parameters can be used. In a similar way as described above, the final polymer properties may be achieved by controlled metering reactor parameters in response to data generated by the Raman analyzer.

EXAMPLES

Laboratory determinations of density (g/cm$^3$) used a compression molded sample, cooled at 15° C. per hour and conditioned for 40 hours at room temperature according to ASTM D1505 and ASTM D1928, procedure C.

Laboratory determinations of melt flow rates were carried out at 190° C. according to ASTM D-1238. $I_{21.6}$ is the "flow index" or melt flow rate of the polymer measured according to ASTM D-1238, condition F, and $I_{2.16}$ is the "melt index" or melt flow rate of the polymer measured according to ASTM D-1238, condition E. The ratio of $I_{21.6}$ to $I_{2.16}$ is the "melt flow ratio" or "MFR".

EXCEED™ 350 is a gas-phase metallocene produced LLDPE ethylene/hexene copolymer with a Melt Index ($I_{2.16}$) of 1.0 g/10 min, and a density of 0.918 g/cm$^3$, available from ExxonMobil Chemical Co., Houston, Tex. The EXCEED™ 350 resin is now marketed as EXCEED™ 3518.

EXCEED™ 357 is a gas-phase metallocene produced LLDPE ethylene/hexene copolymer with a Melt Index ($I_{2.16}$) of 3.4 g/10 min, and a density of 0.917 g/cm$^3$, available from ExxonMobil Chemical Co., Houston, Tex. The EXCEED™ 357 resin is now marketed as EXCEED™ 3518.

ExxonMobil LL-1002 is a gas-phase Ziegler-Natta produced LLDPE ethylene/butene copolymer resin having a Melt Index ($I_{2.16}$) of 2.0 g/10 min, and a density of 0.918 g/cm$^3$, available from ExxonMobil Chemical Co., Houston, Tex.

ExxonMobil LL-1107 is a gas-phase Ziegler-Natta produced LLDPE ethylene/butene copolymer resin having a Melt Index ($I_{2.16}$) of 0.8 g/10 min, and a density of 0.922 g/cm$^3$, available from ExxonMobil Chemical Co., Houston, Tex.

ExxonMobil LL-6100 is a gas-phase Ziegler-Natta produced LLDPE ethylene/butene copolymer resin having a Melt Index ($I_{2.16}$) of 20 g/10 min, and a density of 0.925 g/cm$^3$, available from ExxonMobil Chemical Co., Houston, Tex.

ExxonMobil LL-6101 is a gas-phase Ziegler-Natta produced LLDPE ethyleneibutene copolymer resin having a Melt Index ($I_{2.16}$) of 20 g/10 min, and a density of 0.925 g/cm$^3$, available from ExxonMobil Chemical Co., Houston, Tex.

ExxonMobil LL-6201 is a gas-phase Ziegler-Natta produced LLDPE ethylene/butene copolymer resin having a Melt Index ($I_{2.16}$) of 50 g/10 min, and a density of 0.926 g/cm$^3$, available from ExxonMobil Chemical Co., Houston, Tex.

Examples 1–3

Examples 1–3 were used to show the feasibility of embodiments of the invention. In Examples 1–3, measurements were made in the laboratory, simulating the measurements that would be made on-line in a polymerization reactor.

The Raman system used for Examples 1–3 was a Kaiser Optical Holoprobe Process Raman Analyzer, available from Kaiser Optical Systems, Inc., Ann Arbor, Michigan. The Raman system used a 125 mW diode laser operating at 785 nm, and was equipped with a probe with 2.5 (6.3 cm) inch imaging optics fiber-optically coupled to the instrument, a holographic notch filter, holographic dispersion grating, cooled CCD detector (−40° C.), and computer for analyzer control and data analysis. A more complete description of this commercial instrument can be found in "Electro-Optic, Integrated Optic, and Electronic Technologies for Online Chemical Process Monitoring," *Proceedings SPIE*, vol. 3537, pp. 200–212 (1998), the disclosure of which is incorporated herein by reference for purposes of U.S. patent practice.

Data collection was accomplished by positioning the Raman probe above the surface of a polymer granule sample at a distance of about 2.5 inches (6.3 cm). The probe was fiber optically coupled to the Raman analyzer for both excitation and scattering signals. Data were collected from each sample for three minutes (i.e., signal averaged for 3 minutes). The CCD detector is sensitive to cosmic rays, which can cause spurious signals in array elements. "Cosmic ray checking" is a detector function that checks for these artifacts and discards them. In the following examples, the cosmic ray checking function was used.

Raman spectra were collected over the region of 100 to 3500 cm$^{-1}$. Three consecutive spectra were collected for each sample used. The samples were obtained from either of two gas-phase fluidized bed reactors producing copolymers of ethylene and butene or hexene, using metallocene catalysts. Laboratory measurements of melt index and/or density were also made for each sample.

The data were divided into calibration sets, used to develop the PCA/LWR models, and validation sets, used to evaluate the accuracy of the model. Separate models were developed for a relatively low melt index range, a relatively high melt index range, and density.

Example 1

Low Melt Index Model

Seventy-three polymer samples were evaluated. The samples were divided into a group of 50 used for calibration (model development) and a group of 23 used for model validation. Each sample was a metallocene-catalyzed LLDPE resin, with hexene comonomer, in a melt index range of from about 0.6 to about 1.2 g/10 min. Raman spectra and laboratory melt index measurements were collected as described above.

The lab values of melt index and the Raman spectra of the calibration data set were used to create a locally-weighted regression model for low range melt index, using principal component loadings and principal component scores. The measured melt indexes, predicted melt indexes, and deviations (i.e., deviation of the actual melt index from the prediction of the LWR model) are shown in Table 1.

TABLE 1

| Low MI Calibration | | |
|---|---|---|
| MI (Lab) (dg/min) | MI (Model) (dg/min) | ΔMI[a] (dg/min) |
| 0.678 | 0.663401 | −0.0146 |
| 0.678 | 0.675728 | −0.00227 |
| 0.679 | 0.685591 | 0.006591 |
| 0.679 | 0.653462 | −0.02554 |
| 0.687 | 0.699942 | 0.012942 |
| 0.687 | 0.709433 | 0.022433 |
| 0.696 | 0.700481 | 0.004481 |
| 0.696 | 0.696309 | 0.000309 |
| 0.7 | 0.689811 | −0.01019 |
| 0.7 | 0.694658 | −0.005534 |
| 0.705 | 0.690562 | −0.01444 |
| 0.705 | 0.706591 | 0.001591 |
| 0.706 | 0.69476 | −0.01124 |
| 0.706 | 0.718346 | 0.012346 |
| 0.714 | 0.706535 | −0.00746 |
| 0.714 | 0.703178 | −0.01082 |
| 0.7546 | 0.786602 | 0.032002 |
| 0.7546 | 0.774616 | 0.020016 |
| 0.772 | 0.781622 | 0.009622 |
| 0.772 | 0.779611 | 0.007611 |
| 0.773 | 0.775132 | 0.002132 |
| 0.773 | 0.777378 | 0.004378 |
| 0.808 | 0.800435 | −0.00757 |
| 0.808 | 0.824823 | 0.016823 |
| 0.82 | 0.825021 | 0.005021 |
| 0.82 | 0.823629 | 0.003629 |
| 0.831 | 0.841478 | 0.010478 |
| 0.831 | 0.8089 | −0.0221 |
| 0.84 | 0.819804 | −0.0202 |
| 0.84 | 0.838078 | −0.00192 |
| 0.92 | 0.934314 | 0.014314 |
| 0.92 | 0.93859 | 0.01859 |
| 1.06 | 1.049136 | −0.01086 |
| 1.06 | 1.07161 | 0.01161 |
| 1.07 | 1.080271 | 0.010271 |
| 1.07 | 1.079701 | 0.009701 |
| 1.08 | 1.090437 | 0.010437 |
| 1.08 | 1.055101 | −0.0249 |
| 1.098 | 1.117367 | 0.019367 |
| 1.098 | 1.092972 | −0.00503 |
| 1.1 | 1.083835 | −0.01617 |
| 1.1 | 1.071211 | −0.02879 |
| 1.11 | 1.115756 | 0.005756 |
| 1.11 | 1.106827 | −0.00317 |
| 1.11 | 1.085486 | −0.02451 |
| 1.11 | 1.096664 | −0.01334 |
| 1.15 | 1.142874 | −0.00713 |
| 1.15 | 1.1283 | −0.0217 |
| 1.1811 | 1.200165 | 0.019065 |
| 1.1811 | 1.198869 | 0.017769 |

Model (predicted) MI minus Lab (measured) MI

The Raman spectra of the validation data set were collected, and new principal component scores were calculated from the validation spectra. Using the locally-weighted regression model, the melt index of each validation sample was then calculated. The measured melt indexes, predicted melt indexes, and deviations (i.e., deviation of the actual melt index from the prediction of the LWR model) are shown in Table 2.

TABLE 2

| Low MI Validation | | |
|---|---|---|
| MI (Lab) (dg/min) | MI (Model) (dg/min) | ΔMI[a] (dg/min) |
| 0.55 | 0.561835 | 0.011835 |
| 0.55 | 0.579349 | 0.029349 |
| 0.55 | 0.57315 | 0.02315 |
| 0.616 | 0.654254 | 0.038254 |
| 0.616 | 0.637083 | 0.021083 |
| 0.616 | 0.667328 | 0.051328 |
| 0.622 | 0.6504 | 0.0284 |
| 0.622 | 0.635863 | 0.013863 |
| 0.622 | 0.669156 | 0.047156 |
| 0.679 | 0.644011 | −0.03499 |
| 0.679 | 0.632626 | −0.04637 |
| 0.679 | 0.634522 | −0.04448 |
| 0.883 | 0.802692 | −0.08031 |
| 0.883 | 0.856272 | −0.02673 |
| 0.883 | 0.849839 | −0.03316 |
| 0.95 | 1.083123 | 0.133123 |
| 0.95 | 1.022883 | 0.072883 |
| 0.95 | 1.021329 | 0.071329 |
| 1.065 | 1.006358 | −0.05864 |
| 1.065 | 0.950208 | −0.11479 |
| 1.065 | 0.978949 | −0.08605 |
| 1.142 | 1.14752 | 0.00552 |
| 1.142 | 1.12363 | −0.01837 |

Model (predicted) MI minus Lab (measured) MI

Figure 6A:
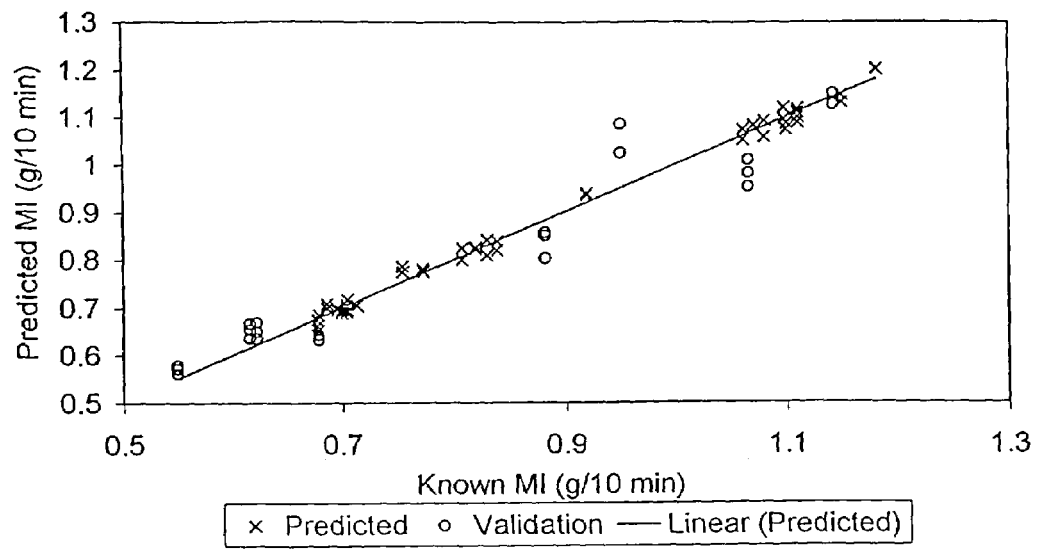
FIGS. 6a and 6b show predicted versus measured melt indices in low and high melt index ranges, respectively, according to Examples 1 and 2.

FIG. 6A depicts the data from Tables 1 and 2 graphically. The line in the Figure is the model prediction. The calculated $R^2$ value was 0.99 for the calibration set, with a standard error of 0.0155, and 0.92 for the validation set, with a standard error of 0.059.

Example 2

High Melt Index Model

An analysis was carried out as in Example 1, using higher melt index samples. Thirty-four polymer samples were evaluated. These samples were used as calibration samples for model development, but a validation subset was not used. Each sample was a metallocene-catalyzed LLDPE resin, with butene comonomer, in a melt index range of from about 4 to about 60 g/10 min. Raman spectra and laboratory melt index measurements were collected as described above.

The lab values of melt index and the Raman spectra of the calibration data set were used to create a locally-weighted regression model for high range melt index, using principal component loadings and principal component scores. The measured melt indexes, predicted melt indexes, and deviations (i.e., deviation of the actual melt index from the prediction of the LWR model) are shown in Table 3.

TABLE 3

High MI Calibration

| MI (Lab) (dg/min) | MI (Model) (dg/min) | ΔMI[a] (dg/min) |
|---|---|---|
| 4.341 | 4.513 | 0.172 |
| 4.341 | 4.467 | 0.126 |
| 8.613 | 8.433 | −0.18 |
| 8.613 | 8.314 | −0.299 |
| 10.499 | 9.978 | −0.521 |
| 10.499 | 10.768 | 0.269 |
| 12.547 | 13.013 | 0.466 |
| 12.547 | 12.971 | 0.424 |
| 18.61 | 17.955 | −0.655 |
| 18.61 | 17.885 | −0.725 |
| 19.81 | 21.009 | 1.199 |
| 19.81 | 20.893 | 1.083 |
| 21.59 | 22.011 | 0.421 |
| 21.59 | 22.314 | 0.724 |
| 22.79 | 22.291 | −0.499 |
| 22.79 | 23.109 | 0.319 |
| 30.68 | 28.212 | −2.468 |
| 30.68 | 29.118 | −1.562 |
| 32.93 | 32.112 | −0.818 |
| 32.93 | 32.459 | −0.471 |
| 33.68 | 34.658 | 0.978 |
| 33.68 | 34.233 | 0.553 |
| 36.6 | 37.216 | 0.616 |
| 36.6 | 36.989 | 0.389 |
| 45.15 | 44.433 | −0.717 |
| 45.15 | 45.001 | −0.149 |
| 48.07 | 48.966 | 0.896 |
| 48.07 | 49.207 | 1.137 |
| 51.41 | 49.879 | −1.531 |
| 51.41 | 50.554 | −0.856 |
| 55.56 | 57.213 | 1.653 |
| 55.56 | 56.667 | 1.107 |
| 57.41 | 57.942 | 0.532 |
| 57.41 | 58.217 | 0.807 |

[a] Model (predicted) MI minus Lab (measured) MI

Figure 6B:
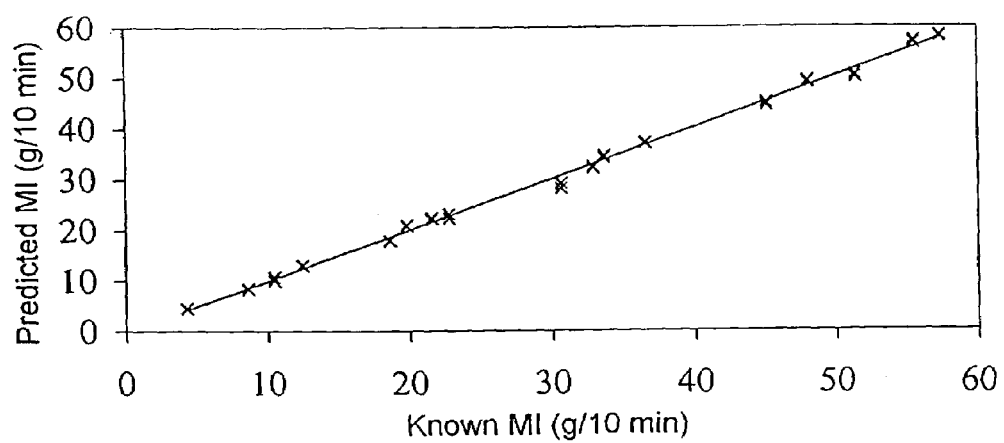

FIG. 6B depicts the data from Table 3 graphically. The line in the Figure is the model prediction. The calculated $R^2$ value was 0.99, with a standard error of 0.91.

Example 3

Density Model

An analysis was carried out as in Example 1, using density rather than melt index as the predicted property. A subset of 22 of the polymer samples used in Example 1 were evaluated. These samples were used as calibration samples for model development, but a validation subset was not used. Each sample was a metallocene-catalyzed LLDPE resin, with hexene comonomer. Raman spectra and laboratory density measurements were collected as described above.

The lab values of density and the Raman spectra of the calibration data set were used to create a locally-weighted regression model for density, using principal component loadings and principal component scores. The measured densities, predicted densities, and deviations (i.e., deviation of the actual density from the prediction of the LWR model) are shown in Table 4.

TABLE 4

Density Calibration

| ρ (Lab) (g/cm³) | ρ (Model) (g/cm³) | ρ[a] (g/cm³) |
|---|---|---|
| 0.9183 | 0.919018 | 0.000718 |
| 0.9183 | 0.919053 | 0.000753 |
| 0.9185 | 0.917859 | −0.00064 |
| 0.9185 | 0.917786 | −0.00071 |
| 0.9195 | 0.918575 | −0.00092 |
| 0.9195 | 0.918499 | −0.001 |
| 0.9196 | 0.919342 | −0.00026 |
| 0.9196 | 0.919943 | 0.000343 |
| 0.9212 | 0.921674 | 0.000474 |
| 0.9212 | 0.921701 | 0.000501 |
| 0.9218 | 0.92193 | 0.00013 |
| 0.9218 | 0.922121 | 0.000321 |
| 0.922 | 0.921901 | −0.000099 |
| 0.922 | 0.922797 | 0.000797 |
| 0.9226 | 0.921872 | −0.00073 |
| 0.9226 | 0.922369 | −0.00023 |
| 0.9244 | 0.924316 | −0.000084 |
| 0.9244 | 0.924075 | −0.00033 |
| 0.9249 | 0.924893 | −0.000007 |
| 0.9249 | 0.924031 | −0.00087 |
| 0.9262 | 0.926252 | 0.000052 |
| 0.9262 | 0.925936 | −0.00026 |

[a] Model (predicted) density minus Lab (measured) density

Figure 7:
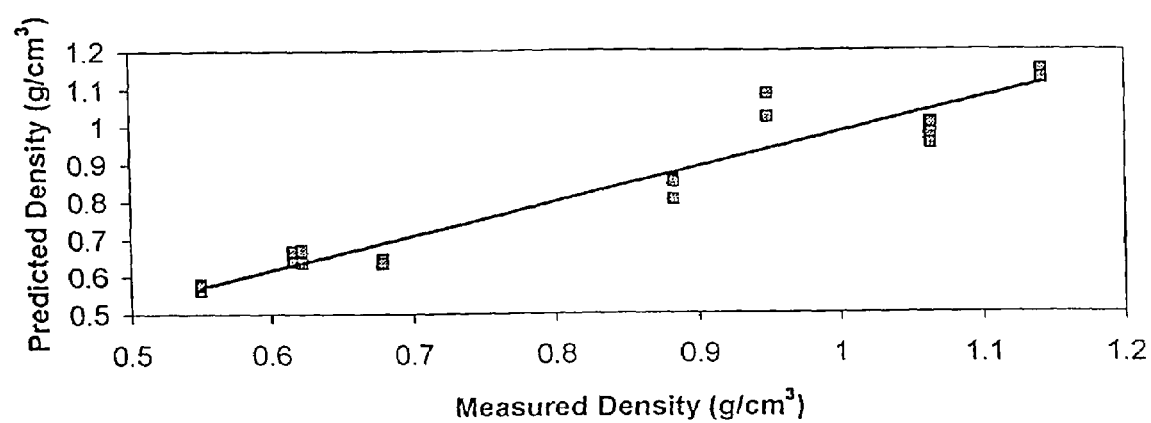
FIG. 7 shows predicted versus measured density according to Example 3.

FIG. 7 depicts the data graphically. The line in the Figure is the model prediction. The calculated $R^2$ value was 0.95, with a standard error of 0.00057.

Examples 4–5

Examples 4–5 demonstrate the effectiveness of the inventive methods on-line in a polymerization reaction system, for melt index determination.

The Raman system used for Examples 4–5 was as described for Examples 1–3, except that the laser was a 200 mW mode-stabilized diode laser operating at 785 nm. Polymer samples from either of two gas-phase fluidized-bed reactors were taken using the sampling system described above.

The data were divided into calibration sets, used to develop the PCA/LWR models, and validation sets, used to evaluate the accuracy of the model. Separate models were developed for a melt index (Examples 4–5) and density (Examples 6–7). In addition, separate models were developed for each of the two gas-phase reactors. The two reactors are denoted "Reactor 1" and "Reactor 2" below.

Example 4

Melt Index Model, Reactor 1

Two hundred eighty-five polymer samples were evaluated. The samples were divided into a group of 216 used for calibration (model development) and a group of 69 used for model validation. Each sample was a metallocene-catalyzed LLDPE resin, in a melt index range of from less than 1 to about 15 g/10 min. Raman spectra and laboratory melt index measurements were collected as described above.

The lab values of melt index and the Raman spectra of the calibration data set were used to create a locally-weighted regression model for melt index, using principal component loadings and principal component scores. The measured melt indexes and predicted melt indexes are shown in Tables 5A–5B. The deviations are not shown in the table, but are readily calculated from the tabulated data. The data are shown in the order taken (by column, within each table), to illustrate the effectiveness of the model under changing polymer conditions. A symbol "Vn" before an entry indicates that the nth set of validation spectra were taken before the marked entry, as shown by the corresponding notation in Table 6. Table 5B is a continuation of Table 5A.

TABLE 5A

MI Calibration, Reactor 1

| MI (Lab) (dg/min) | MI (Model) (dg/min) |
|---|---|
| 4.997 | 5.013 |
| 4.413 | 4.390 |
| 4.559 | 4.410 |
| 3.511 | 3.633 |
| 3.481 | 3.521 |
| 3.315 | 3.391 |
| 3.301 | 3.286 |
| 3.369 | 3.211 |
| 3.460 | 3.607 |
| 3.391 | 3.481 |
| 3.380 | 3.301 |
| 3.523 | 3.629 |
| 3.370 | 3.294 |
| 3.537 | 3.522 |
| 3.534 | 3.559 |
| 3.432 | 3.407 |
| 3.518 | 3.671 |
| 3.555 | 3.562 |
| 3.380 | 3.299 |
| 3.320 | 3.308 |
| 3.470 | 3.523 |
| 3.380 | 3.405 |
| 3.380 | 3.277 |
| 3.370 | 3.328 |
| 3.370 | 3.400 |
| 3.354 | 3.290 |
| 3.354 | 3.540 |
| 3.523 | 3.327 |
| 3.523 | 3.473 |
| 3.491 | 3.551 |
| 3.582 | 3.613 |
| 3.582 | 3.612 |
| 3.493 | 3.464 |
| 3.493 | 3.375 |
| 3.523 | 3.596 |
| 3.506 | 3.483 |
| 3.506 | 3.440 |
| 3.554 | 3.401 |
| 3.554 | 3.474 |
| 3.541 | 3.540 |
| 3.576 | 3.713 |
| 3.576 | 3.679 |
| 3.630 | 3.664 |
| 3.630 | 3.664 |
| 3.626 | 3.563 |
| 3.618 | 3.652 |
| 3.346 | 3.257 |
| 3.409 | 3.399 |
| 3.409 | 3.426 |
| (V1)3.411 | 3.342 |
| 3.572 | 3.743 |
| 2.351 | 2.402 |
| 1.544 | 1.574 |
| 1.348 | 1.364 |
| 1.163 | 1.140 |
| 1.106 | 1.095 |
| 1.072 | 1.100 |
| 1.098 | 1.103 |
| 1.071 | 1.110 |
| 0.987 | 0.971 |
| 1.009 | 0.994 |
| 1.005 | 0.998 |
| 0.978 | 0.980 |
| 1.009 | 1.010 |
| 0.991 | 1.039 |

TABLE 5A-continued

MI Calibration, Reactor 1

| MI (Lab) (dg/min) | MI (Model) (dg/min) |
|---|---|
| 1.002 | 0.991 |
| 1.038 | 1.094 |
| 1.035 | 1.000 |
| 1.016 | 1.023 |
| 0.940 | 0.932 |
| 0.970 | 0.980 |
| 0.980 | 0.979 |
| 0.967 | 0.973 |
| 0.952 | 0.961 |
| 0.956 | 0.977 |
| 0.969 | 0.940 |
| 0.973 | 0.994 |
| 0.946 | 0.980 |
| 0.972 | 0.960 |
| 1.135 | 1.083 |
| 1.188 | 1.209 |
| 1.182 | 1.231 |
| 1.130 | 1.104 |
| 1.138 | 1.193 |
| 1.015 | 0.996 |
| 0.977 | 0.967 |
| 0.965 | 0.973 |
| 0.970 | 0.980 |
| 0.985 | 0.990 |
| 0.952 | 0.962 |
| 0.923 | 0.918 |
| 0.921 | 0.900 |
| 1.017 | 0.981 |
| 1.005 | 1.061 |
| 1.010 | 1.012 |
| 1.030 | 1.078 |
| 0.986 | 0.979 |
| 0.944 | 0.937 |
| 0.947 | 0.953 |
| 0.955 | 0.972 |
| 0.932 | 0.928 |
| 0.947 | 0.944 |
| 0.984 | 0.990 |
| 0.972 | 0.994 |
| 0.998 | 0.990 |
| 0.991 | 1.039 |
| 1.060 | 1.004 |
| 1.041 | 1.013 |

TABLE 5B

MI Calibration, Reactor 1, continued

| MI (Lab) (dg/min) | MI (Model) (dg/min) |
|---|---|
| 0.989 | 1.000 |
| 0.921 | 0.910 |
| 0.908 | 0.880 |
| 0.951 | 0.962 |
| 0.976 | 0.990 |
| 0.965 | 0.941 |
| 0.970 | 0.992 |
| 0.966 | 1.002 |
| 0.998 | 1.092 |
| 0.983 | 0.963 |
| 0.985 | 0.973 |
| 0.990 | 0.999 |
| 0.990 | 1.024 |
| 0.993 | 1.003 |
| 0.968 | 0.982 |
| 0.997 | 0.971 |
| 1.006 | 0.982 |
| (V2)0.939 | 0.926 |
| 0.966 | 0.953 |
| 0.992 | 1.017 |

TABLE 5B-continued

MI Calibration, Reactor 1, continued

| MI (Lab) (dg/min) | MI (Model) (dg/min) |
|---|---|
| 0.989 | 0.993 |
| 0.951 | 0.937 |
| 1.030 | 1.018 |
| 1.000 | 1.005 |
| 0.959 | 0.939 |
| 0.954 | 0.957 |
| 0.940 | 0.910 |
| 0.985 | 0.991 |
| 0.980 | 0.991 |
| 0.955 | 0.931 |
| 0.930 | 0.909 |
| 0.910 | 0.891 |
| 0.940 | 0.963 |
| 0.980 | 1.003 |
| 0.980 | 0.993 |
| 0.960 | 0.968 |
| 0.938 | 0.942 |
| 0.988 | 0.960 |
| 1.006 | 1.039 |
| 0.982 | 1.002 |
| 0.946 | 0.978 |
| 0.964 | 0.930 |
| 1.010 | 0.962 |
| 1.030 | 1.082 |
| 1.040 | 1.019 |
| 1.080 | 1.103 |
| 1.020 | 1.031 |
| 1.040 | 1.039 |
| (V3) 1.061 | 1.092 |
| 1.546 | 1.552 |
| 2.043 | 1.993 |
| 2.381 | 2.402 |
| 2.751 | 2.772 |
| 3.054 | 2.994 |
| 3.414 | 3.540 |
| 3.342 | 3.254 |
| 3.550 | 3.453 |
| 3.580 | 3.429 |
| 3.550 | 3.445 |
| 3.610 | 3.454 |
| 3.528 | 3.310 |
| 3.246 | 3.152 |
| 3.523 | 3.391 |
| 3.620 | 3.662 |
| 3.691 | 3.604 |
| 3.713 | 3.700 |
| 3.451 | 3.619 |
| 3.439 | 3.293 |
| 3.501 | 3.701 |
| 3.263 | 3.331 |
| 3.433 | 3.383 |
| 3.477 | 3.579 |
| 3.490 | 3.311 |
| 3.528 | 3.466 |
| 3.538 | 3.555 |
| 3.592 | 3.403 |
| 3.372 | 3.441 |
| (V4) 3.580 | 3.726 |
| 3.259 | 3.109 |
| 3.302 | 3.319 |
| 3.437 | 3.572 |
| 3.397 | 3.429 |
| 3.449 | 3.401 |
| 3.513 | 3.329 |
| 3.771 | 3.702 |
| 3.986 | 3.918 |
| 4.575 | 4.428 |
| 5.000 | 4.892 |
| 6.054 | 6.203 |
| 7.452 | 7.624 |
| 8.392 | 8.012 |
| 10.630 | 10.171 |
| 10.630 | 10.171 |
| 12.530 | 12.779 |
| 13.110 | 13.671 |
| 13.879 | 13.698 |
| 13.952 | 13.498 |
| 13.627 | 13.593 |
| 13.295 | 12.998 |
| 13.393 | 13.876 |
| 13.146 | 13.029 |
| 12.810 | 13.014 |
| 11.989 | 11.903 |
| 10.670 | 11.003 |
| 12.181 | 12.292 |
| 12.711 | 12.625 |
| 1.120 | 1.204 |
| 1.002 | 1.002 |

The Raman spectra of the validation data set were also collected, and new principal component scores were calculated from the validation sample was locally-weighted regression model, the melt index of each validation sample was then calculated. The measured and predicted melt indexes are shown in Table 6. Acquisition of the validation spectra was interspersed with acquisition of the calibration spectra, at the corresponding "Vn" positions.

TABLE 6

MI Validation, Reactor 1

| MI (Lab) (dg/min) | MI (Model) (dg/min) |
|---|---|
| V1: 3.471 | 3.514 |
| 3.443 | 3.503 |
| 3.438 | 3.371 |
| 3.493 | 3.421 |
| 3.417 | 3.561 |
| 3.354 | 3.365 |
| 3.454 | 3.604 |
| 3.531 | 3.594 |
| 3.557 | 3.500 |
| 3.521 | 3.498 |
| 3.440 | 3.352 |
| 3.507 | 3.521 |
| 3.596 | 3.569 |
| 3.659 | 3.623 |
| 3.554 | 3.648 |
| 3.565 | 3.662 |
| 3.605 | 3.807 |
| 3.573 | 3.531 |
| 3.456 | 3.604 |
| 3.501 | 3.586 |
| 3.500 | 3.398 |
| V2: 0.980 | 0.998 |
| 0.966 | 0.982 |
| 0.965 | 0.991 |
| 1.000 | 0.973 |
| 0.995 | 0.999 |
| 0.964 | 0.952 |
| 0.934 | 0.943 |
| 0.946 | 0.967 |
| 0.943 | 0.920 |
| 0.928 | 0.892 |
| 0.931 | 0.950 |
| 0.967 | 0.972 |
| 0.949 | 0.957 |
| 1.025 | 0.980 |
| 1.029 | 1.089 |
| 1.032 | 1.012 |
| 1.025 | 1.034 |
| 0.999 | 1.004 |

TABLE 6-continued

MI Validation, Reactor 1

| MI (Lab) (dg/min) | MI (Model) (dg/min) |
|---|---|
| 0.995 | 0.970 |
| 1.009 | 0.998 |
| 1.035 | 1.029 |
| 1.048 | 1.011 |
| 1.012 | 1.029 |
| V3: 1.095 | 1.118 |
| 1.114 | 1.092 |
| 0.933 | 0.960 |
| 0.859 | 0.811 |
| 0.934 | 0.903 |
| 0.980 | 1.011 |
| 0.910 | 0.880 |
| 0.890 | 0.920 |
| 0.900 | 0.899 |
| 0.970 | 0.992 |
| 0.980 | 0.962 |
| 0.990 | 1.053 |
| V4: 3.470 | 3.625 |
| 3.620 | 3.772 |
| 3.420 | 3.400 |
| 3.504 | 3.387 |
| 3.682 | 3.598 |
| 3.597 | 3.784 |
| 3.531 | 3.724 |
| 3.399 | 3.412 |
| 3.590 | 3.498 |
| 3.520 | 3.500 |
| 3.431 | 3.548 |
| 3.391 | 3.293 |
| 3.288 | 3.412 |

Figure 8A:
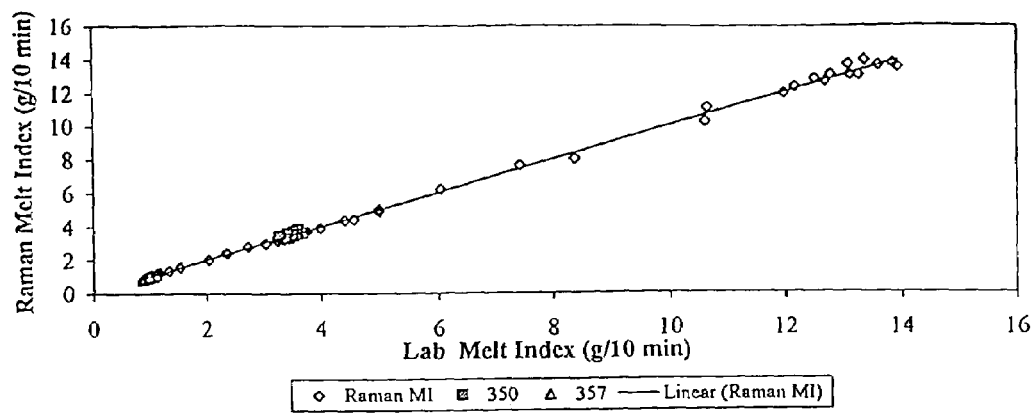
FIGS. 8a and 8b show predicted versus measured melt indices from on-man Raman analyses in metallocene- and Ziegler-Natta-catalyzed reactions, respectively, according to Examples 4–5.

FIG. 8A depicts the data from Tables 5A, 5B and 6 graphically. The line in the Figure is the model prediction. The calculated $R^2$ value was 0.999, with a standard error of 2.78%.

Example 5

Melt Index Model, Reactor 2

The procedure described in Example 4 was followed, except as noted, sampling this time from the Reactor 2 polymer. Two hundred ninety-one polymer samples were evaluated. The samples were divided into a group of 266 used for calibration (model development) and a group of 25 used for model validation. Each sample was a Ziegler-Natta-catalyzed LLDPE resin, in a melt index range of from less than 1 to about 60 g/10 min. Raman spectra and laboratory melt index measurements were collected as described above.

The lab values of melt index and the Raman spectra of the calibration data set were used to create a locally-weighted regression model for melt index, using principal component loadings and principal component scores. The measured melt indexes and predicted melt indexes are shown in Tables 7A–7B. The deviations are not shown in the table, but are readily calculated from the tabulated data. The data are shown in the order taken (by column, within each table), to illustrate the effectiveness of the model under changing polymer conditions. A symbol "Vn" before an entry indicates that the nth set of validation spectra were taken before the marked entry, as shown by the corresponding notation in Table 8. Table 7B is a continuation of Table 7A. In Tables 7A and 7B, the units of melt index (MI) are dg/min.

TABLE 7A

MI Calibration, Reactor 2

| MI (Lab) | MI (Model) |
|---|---|
| 0.678 | 0.669 |
| 2.008 | 2.105 |
| 1.410 | 1.376 |
| 0.992 | 0.988 |
| 0.832 | 0.859 |
| 0.758 | 0.780 |
| 0.712 | 0.688 |
| 0.673 | 0.690 |
| 0.670 | 0.710 |
| 0.721 | 0.690 |
| 0.753 | 0.774 |
| 0.751 | 0.779 |
| 0.780 | 0.810 |
| 0.811 | 0.779 |
| 0.792 | 0.810 |
| 0.782 | 0.750 |
| 0.753 | 0.775 |
| 0.767 | 0.798 |
| 0.706 | 0.700 |
| 0.878 | 0.892 |
| 0.858 | 0.823 |
| 0.817 | 0.829 |
| 0.857 | 0.802 |
| 0.849 | 0.836 |
| 0.779 | 0.750 |
| 0.765 | 0.770 |
| 0.742 | 0.727 |
| 0.806 | 0.800 |
| 0.810 | 0.801 |
| 0.827 | 0.839 |
| 0.778 | 0.789 |
| 0.796 | 0.763 |
| 0.768 | 0.712 |
| 0.899 | 0.912 |
| 0.946 | 0.963 |
| 0.965 | 1.002 |
| 0.890 | 0.862 |
| 0.837 | 0.843 |
| V1 17.580 | 18.001 |
| 19.194 | 18.899 |
| 20.280 | 21.021 |
| 19.588 | 20.091 |
| 19.732 | 18.979 |
| 20.910 | 22.098 |
| 20.070 | 20.473 |
| 19.800 | 19.070 |
| 20.900 | 20.078 |
| 22.080 | 21.874 |
| 20.080 | 19.659 |
| 19.616 | 19.223 |
| 19.829 | 19.629 |
| 17.090 | 17.651 |
| 18.086 | 17.888 |
| 17.638 | 16.844 |
| 18.637 | 17.974 |
| 20.010 | 20.119 |
| 19.568 | 19.103 |
| V2 27.270 | 27.906 |
| 42.780 | 43.099 |
| 48.560 | 47.956 |
| 51.950 | 52.302 |
| 51.270 | 51.037 |
| 49.950 | 50.119 |
| 45.610 | 46.117 |
| 47.440 | 46.938 |
| 53.620 | 52.476 |
| 55.210 | 54.998 |
| 50.010 | 49.483 |
| 44.040 | 44.884 |
| 42.780 | 41.009 |
| 47.940 | 47.444 |
| 53.720 | 52.798 |
| 53.370 | 54.007 |
| 52.750 | 52.559 |
| 50.660 | 51.032 |

TABLE 7A-continued

MI Calibration, Reactor 2

| MI (Lab) | MI (Model) |
|---|---|
| 51.720 | 50.759 |
| 48.530 | 47.667 |
| 44.160 | 45.221 |
| 47.000 | 46.821 |
| 53.370 | 54.202 |
| 41.750 | 40.512 |
| 48.360 | 49.848 |
| 50.890 | 49.111 |
| 43.810 | 43.084 |
| 43.850 | 44.106 |
| 46.200 | 47.485 |
| 48.220 | 48.944 |
| 49.950 | 49.004 |
| 49.590 | 50.672 |
| [V3]41.540 | 41.094 |
| 21.320 | 22.445 |
| 17.983 | 18.241 |
| 17.233 | 16.869 |
| 19.677 | 19.311 |
| 19.063 | 19.921 |
| 19.919 | 19.107 |
| 21.510 | 21.444 |
| 20.840 | 20.771 |
| 20.500 | 19.295 |
| 20.230 | 21.011 |
| 21.230 | 20.659 |
| 21.670 | 20.997 |
| 20.590 | 21.264 |
| 23.140 | 22.784 |
| 22.460 | 21.997 |
| 20.640 | 20.883 |
| 21.260 | 20.799 |
| 19.856 | 20.231 |
| 22.150 | 21.888 |
| 21.230 | 20.465 |
| 20.440 | 21.055 |
| 20.370 | 20.477 |
| 19.974 | 20.077 |
| 22.930 | 22.374 |
| [V4]7.250 | 7.442 |
| 3.790 | 3.801 |
| 2.460 | 2.404 |
| 2.090 | 1.998 |
| 2.298 | 2.303 |
| 1.947 | 1.887 |
| 1.830 | 1.867 |
| 2.059 | 1.978 |
| 2.131 | 1.992 |
| 2.051 | 2.119 |
| 2.170 | 2.085 |
| 2.090 | 2.177 |
| 2.160 | 2.285 |
| 2.130 | 1.951 |
| 2.050 | 1.989 |
| 2.000 | 1.999 |
| 1.917 | 1.974 |
| 1.974 | 2.101 |
| 2.064 | 2.001 |
| 2.077 | 1.985 |
| 2.035 | 2.103 |
| 2.007 | 2.110 |
| 1.980 | 2.004 |
| 1.950 | 1.891 |
| 1.880 | 1.871 |
| 1.990 | 2.109 |
| 2.230 | 2.190 |
| 2.100 | 1.962 |
| 1.998 | 2.119 |
| 1.910 | 1.967 |

TABLE 7B

MI Calibration, Reactor 2, continued

| MI (Lab) | MI (Model) |
|---|---|
| 2.204 | 2.187 |
| 2.350 | 2.410 |
| 2.201 | 2.177 |
| 2.050 | 1.939 |
| 2.120 | 2.098 |
| 2.000 | 2.079 |
| 2.040 | 2.101 |
| 2.100 | 2.008 |
| 2.040 | 2.113 |
| 1.950 | 1.889 |
| [V5]0.945 | 0.902 |
| 0.970 | 0.978 |
| 0.965 | 0.954 |
| 1.281 | 1.299 |
| 1.445 | 1.455 |
| 1.502 | 1.552 |
| 1.373 | 1.299 |
| 1.365 | 1.399 |
| 1.420 | 1.390 |
| 1.462 | 1.442 |
| 1.674 | 1.739 |
| 1.868 | 1.920 |
| 2.168 | 2.122 |
| 1.979 | 1.948 |
| 3.279 | 3.309 |
| 0.969 | 1.002 |
| 1.018 | 1.040 |
| 1.078 | 1.039 |
| 1.009 | 0.988 |
| 1.034 | 0.992 |
| 1.005 | 1.056 |
| 0.974 | 0.980 |
| 0.992 | 1.006 |
| 0.924 | 0.898 |
| 0.983 | 0.978 |
| 0.970 | 0.952 |
| 1.079 | 1.108 |
| 1.077 | 0.997 |
| 1.093 | 1.121 |
| 1.108 | 1.110 |
| 1.071 | 0.997 |
| 1.013 | 0.999 |
| 0.980 | 0.980 |
| 1.061 | 1.046 |
| 1.005 | 1.018 |
| 0.961 | 0.967 |
| 1.005 | 0.997 |
| 0.980 | 0.977 |
| 0.864 | 0.877 |
| 0.891 | 0.903 |
| 0.996 | 1.043 |
| 1.054 | 1.044 |
| 1.017 | 1.009 |
| 1.023 | 0.995 |
| 2.079 | 1.997 |
| 1.963 | 2.047 |
| 1.963 | 2.065 |
| 1.880 | 1.841 |
| 2.070 | 2.109 |
| 2.180 | 2.116 |
| 2.290 | 2.341 |
| 2.150 | 2.098 |
| 2.010 | 1.992 |
| 1.346 | 1.375 |
| 0.945 | 0.972 |
| 0.700 | 0.700 |
| 0.825 | 0.830 |
| 0.843 | 0.852 |
| 0.792 | 0.804 |
| 0.791 | 0.801 |
| 0.796 | 0.799 |
| 0.745 | 0.756 |
| 0.777 | 0.791 |
| 0.734 | 0.720 |
| 0.711 | 0.720 |

TABLE 7B-continued

MI Calibration, Reactor 2, continued

| MI (Lab) | MI (Model) |
|---|---|
| 0.763 | 0.777 |
| 0.778 | 0.801 |
| 0.685 | 0.673 |
| 0.769 | 0.776 |
| 0.760 | 0.743 |
| 0.738 | 0.750 |
| 0.726 | 0.701 |
| 0.719 | 0.742 |
| 0.706 | 0.688 |
| 0.781 | 0.743 |
| 0.797 | 0.822 |
| 0.750 | 0.770 |
| 0.779 | 0.788 |
| 0.806 | 0.810 |
| 0.768 | 0.773 |
| 0.896 | 0.910 |
| 1.142 | 1.172 |
| 1.176 | 1.149 |
| 1.242 | 1.219 |
| 1.320 | 1.331 |
| 1.396 | 1.387 |
| 1.480 | 1.520 |
| 1.594 | 1.554 |
| 1.525 | 1.501 |
| 1.576 | 1.629 |
| 1.664 | 1.711 |
| 1.544 | 1.557 |
| 1.962 | 1.891 |
| 5.093 | 4.894 |
| 9.130 | 9.297 |
| 12.063 | 11.999 |
| 13.815 | 13.684 |
| 13.262 | 13.555 |
| 16.134 | 16.643 |
| 15.180 | 15.322 |
| 15.845 | 16.015 |
| 15.730 | 15.926 |
| 12.221 | 12.442 |
| 11.531 | 11.735 |
| 12.532 | 12.221 |
| 12.358 | 12.471 |
| 12.538 | 12.882 |
| 12.549 | 12.555 |
| 12.948 | 12.507 |
| 13.413 | 13.119 |
| 12.543 | 12.629 |
| 12.500 | 12.409 |
| 12.111 | 12.427 |
| 11.957 | 11.883 |

The Raman spectra of the validation data set were also collected, and new principal component scores were calculated from the validation spectra. Using the locally-weighted regression model, the melt index of each validation sample was then calculated. The measured and predicted melt indexes are shown in Table 8. Acquisition of the validation spectra was interspersed with acquisition of the calibration spectra, at the corresponding "Vn" positions.

TABLE 8

MI Validation, Reactor 2

| MI (Lab) (dg/min) | MI (Model) (dg/min) |
|---|---|
| V1: 0.733 | 0.771 |
| 0.754 | 0.782 |
| 0.798 | 0.810 |
| 0.727 | 0.718 |
| 0.721 | 0.750 |

TABLE 8-continued

MI Validation, Reactor 2

| MI (Lab) (dg/min) | MI (Model) (dg/min) |
|---|---|
| V2: 17.649 | 18.223 |
| 18.399 | 18.519 |
| 19.844 | 19.492 |
| 21.480 | 21.018 |
| 17.291 | 17.738 |
| 17.896 | 18.229 |
| 20.620 | 20.046 |
| V3: 52.180 | 51.199 |
| 52.020 | 54.219 |
| V4: 24.880 | 24.521 |
| 20.760 | 20.008 |
| 18.667 | 18.903 |
| 16.682 | 16.822 |
| 23.390 | 22.991 |
| V5: 1.907 | 1.915 |
| 1.908 | 1.946 |
| 1.958 | 1.976 |
| 1.902 | 1.911 |
| 1.930 | 1.979 |
| 1.930 | 1.947 |

Figure 8B:
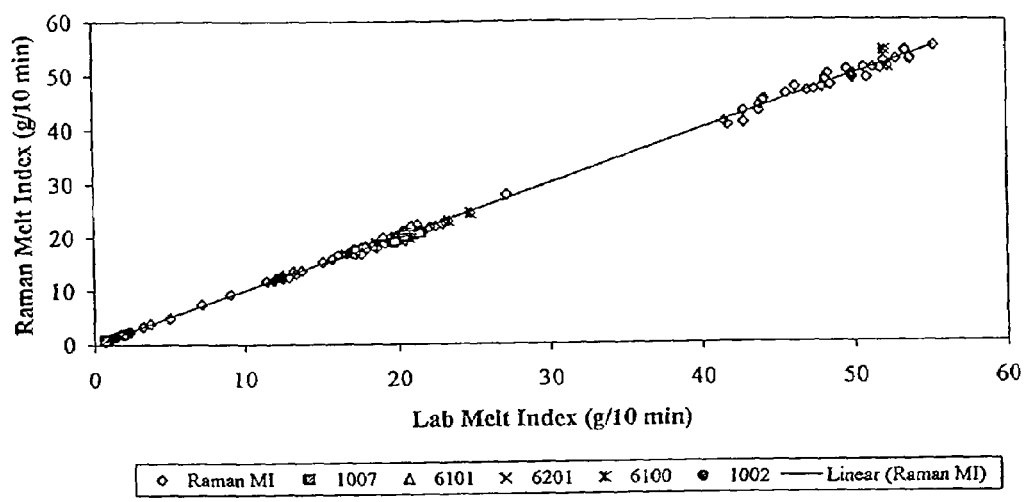

FIG. 8B depicts the data from Tables 7A, 7B and 8 graphically. The line in the Figure is the model prediction. The calculated $R^2$ value was 0.997, with a standard error of 2.86%.

Examples 6–7

Examples 6–7 demonstrate the effectiveness of the inventive methods on-line in a polymerization reaction system, for density determination.

The measurements were carried out as described above in connection with Examples 4–5, except that a PCA/LWR model was developed for density. The samples used, and spectra acquired, are a subset of those of Examples 4–5. Laboratory measurements of density were made on the samples in addition to the melt index measurements described above.

Example 6

Density Model, Reactor 1

One hundred forty-six polymer samples were evaluated. The samples were divided into a group of 109 used for calibration (model development) and a group of 37 used for model validation. Each sample was a metallocene-catalyzed LLDPE resin, in a density range of from about 0.912 to about 0.921 g/cm$^3$. Raman spectra and laboratory density measurements were collected as described above.

The lab values of density and the Raman spectra of the calibration data set were used to create a locally-weighted regression model for density, using principal component loadings and principal component scores. The measured densities and predicted densities are shown in Table 9. The deviations are not shown in the table, but are readily calculated from the tabulated data. The data are shown in the order taken (by column, within each table), to illustrate the effectiveness of the model under changing polymer conditions. A symbol "Vn" before an entry indicates that the nth set of validation spectra were taken before the marked entry, as shown by the corresponding notation in Table 10.

TABLE 9

Density (ρ, g/cm³) Calibration, Reactor 1

| ρ(Lab) | ρ(Model) |
|---|---|
| 0.9202 | 0.9203 |
| 0.9203 | 0.9199 |
| 0.9188 | 0.9186 |
| 0.9202 | 0.9200 |
| 0.9196 | 0.9191 |
| 0.9196 | 0.9195 |
| 0.9195 | 0.9196 |
| 0.9190 | 0.9195 |
| 0.9192 | 0.9187 |
| 0.9195 | 0.9193 |
| 0.9195 | 0.9199 |
| 0.9190 | 0.9194 |
| 0.9190 | 0.9184 |
| 0.9187 | 0.9184 |
| 0.9187 | 0.9190 |
| 0.9188 | 0.9190 |
| 0.9196 | 0.9192 |
| 0.9196 | 0.9195 |
| 0.9202 | 0.9196 |
| 0.9202 | 0.9202 |
| 0.9207 | 0.9204 |
| 0.9200 | 0.9199 |
| 0.9200 | 0.9199 |
| 0.9197 | 0.9200 |
| 0.9195 | 0.9200 |
| 0.9195 | 0.9193 |
| v1 0.9195 | 0.9199 |
| 0.9192 | 0.9187 |
| 0.9160 | 0.9161 |
| 0.9155 | 0.9157 |
| 0.9164 | 0.9159 |
| 0.9167 | 0.9171 |
| 0.9162 | 0.9165 |
| 0.9156 | 0.9153 |
| 0.9156 | 0.9160 |
| 0.9162 | 0.9165 |
| 0.9159 | 0.9162 |
| 0.9158 | 0.9159 |
| 0.9153 | 0.9154 |
| 0.9161 | 0.9162 |
| 0.9189 | 0.9186 |
| 0.9201 | 0.9205 |
| 0.9202 | 0.9204 |
| 0.9201 | 0.9199 |
| 0.9208 | 0.9208 |
| 0.9201 | 0.9202 |
| 0.9164 | 0.9166 |
| 0.9158 | 0.9162 |
| 0.9160 | 0.9158 |
| 0.9159 | 0.9163 |
| 0.9157 | 0.9160 |
| 0.9157 | 0.9156 |
| 0.9159 | 0.9157 |
| 0.9157 | 0.9156 |
| 0.9161 | 0.9156 |
| 0.9160 | 0.9163 |
| 0.9159 | 0.9154 |
| 0.9155 | 0.9158 |
| 0.9149 | 0.9146 |
| 0.9156 | 0.9153 |
| 0.9164 | 0.9162 |
| 0.9160 | 0.9164 |
| 0.9162 | 0.9164 |
| v2 0.9153 | 0.9155 |
| 0.9160 | 0.9163 |
| 0.9158 | 0.9161 |
| 0.9154 | 0.9151 |
| 0.9157 | 0.9157 |
| 0.9149 | 0.9145 |
| 0.9153 | 0.9154 |
| 0.9161 | 0.9165 |
| 0.9150 | 0.9153 |
| 0.9155 | 0.9152 |
| 0.9150 | 0.9151 |
| 0.9151 | 0.9150 |

TABLE 9-continued

Density (ρ, g/cm³) Calibration, Reactor 1

| ρ(Lab) | ρ(Model) |
|---|---|
| 0.9158 | 0.9158 |
| 0.9155 | 0.9157 |
| v3 0.9155 | 0.9159 |
| 0.9186 | 0.9190 |
| 0.9181 | 0.9184 |
| 0.9193 | 0.9195 |
| 0.9191 | 0.9194 |
| 0.9181 | 0.9182 |
| 0.9169 | 0.9170 |
| 0.9189 | 0.9190 |
| 0.9181 | 0.9180 |
| 0.9182 | 0.9184 |
| 0.9186 | 0.9185 |
| 0.9188 | 0.9192 |
| 0.9186 | 0.9181 |
| 0.9184 | 0.9185 |
| v4 0.9194 | 0.9197 |
| 0.9188 | 0.9186 |
| 0.9187 | 0.9185 |
| 0.9180 | 0.9180 |
| 0.9144 | 0.9147 |
| 0.9128 | 0.9130 |
| 0.9130 | 0.9133 |
| 0.9135 | 0.9133 |
| 0.9141 | 0.9143 |
| 0.9149 | 0.9151 |
| 0.9149 | 0.9151 |
| 0.9163 | 0.9164 |
| 0.9167 | 0.9164 |
| 0.9168 | 0.9170 |
| 0.9168 | 0.9173 |
| 0.9155 | 0.9161 |
| 0.9166 | 0.9167 |
| 0.9173 | 0.9175 |

The Raman spectra of the validation data set were also collected, and new principal component scores were calculated from the validation spectra. Using the locally-weighted regression model, the density of each validation sample was then calculated. The measured and predicted densities are shown in Table 10. Acquisition of the validation spectra was interspersed with acquisition of the calibration spectra, at the corresponding "Vn" positions.

TABLE 10

Density (ρ, g/cm³) Validation, Reactor 1

| ρ(Lab) | ρ(Model) |
|---|---|
| V1: 0.9199 | 0.9202 |
| 0.9205 | 0.9202 |
| 0.9205 | 0.9207 |
| 0.9199 | 0.9198 |
| 0.9200 | 0.9198 |
| 0.9196 | 0.9195 |
| 0.9200 | 0.9199 |
| 0.9198 | 0.9201 |
| 0.9190 | 0.9187 |
| 0.9195 | 0.9192 |
| V2: 0.9159 | 0.9161 |
| 0.9188 | 0.9188 |
| 0.9159 | 0.9161 |
| 0.9160 | 0.9159 |
| 0.9155 | 0.9152 |
| 0.9158 | 0.9155 |
| 0.9157 | 0.9153 |
| 0.9158 | 0.9158 |
| 0.9157 | 0.9154 |
| 0.9158 | 0.9156 |
| 0.9158 | 0.9153 |

TABLE 10-continued

Density (ρ, g/cm³) Validation, Reactor 1

| ρ(Lab) | ρ(Model) |
|---|---|
| V3: 0.9157 | 0.9160 |
| 0.9149 | 0.9150 |
| 0.9168 | 0.9168 |
| 0.9149 | 0.9146 |
| 0.9150 | 0.9153 |
| 0.9149 | 0.9147 |
| V4: 0.9193 | 0.9191 |
| 0.9182 | 0.9184 |
| 0.9192 | 0.9193 |
| 0.9197 | 0.9196 |
| 0.9196 | 0.9200 |
| 0.9195 | 0.9196 |
| 0.9189 | 0.9185 |
| 0.9192 | 0.9192 |
| 0.9198 | 0.9197 |
| 0.9192 | 0.9193 |

Figure 9A:
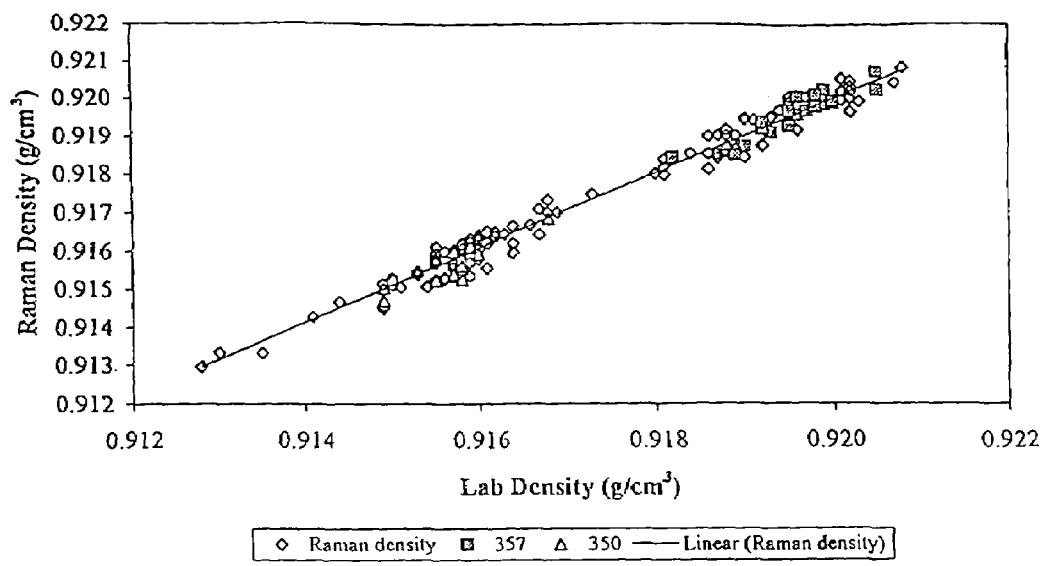
FIGS. 9a and 9b show predicted versus measured density from on-line Raman analyses in metallocene- and Ziegler-Natta-catalyzed reactions, respectively, according to Examples 6–7.

FIG. 9A depicts the data from Tables 9 and 10 graphically. The line in the Figure is the model prediction. The calculated $R^2$ value was 0.978, with a standard error of 0.00028 g/cm³.

Example 7

Density Model, Reactor 2

The procedure described in Example 6 was followed, except as noted, sampling this time from the Reactor 2 polymer. One hundred sixty-four polymer samples were evaluated. The samples were divided into a group of 151 used for calibration (model development) and a group of 13 used for model validation. Each sample was a Ziegler-Natta-catalyzed LLDPE resin, in a density range of from about 0.916 to about 0.927 g/cm³. Raman spectra and laboratory density measurements were collected as described above.

The lab values of density and the Raman spectra of the calibration data set were used to create a locally-weighted regression model for density, using principal component loadings and principal component scores. The measured densities and predicted densities are shown in Tables 11A–11B. The deviations are not shown in the table, but are readily calculated from the tabulated data. The data are shown in the order taken (by column, within each table), to illustrate the effectiveness of the model under changing polymer conditions. A symbol "Vn" before an entry indicates that the nth set of validation spectra were taken before the marked entry, as shown by the corresponding notation in Table 12. Table 11B is a continuation of Table 11A.

TABLE 11A

Density (ρ, g/cm³) Calibration, Reactor 2

| ρ(Lab) | ρ(Model) |
|---|---|
| 0.9182 | 0.9182 |
| 0.9180 | 0.9184 |
| 0.9207 | 0.9209 |
| 0.9220 | 0.9225 |
| 0.9220 | 0.9221 |
| 0.9220 | 0.9217 |
| 0.9218 | 0.9219 |
| 0.9218 | 0.9219 |
| 0.9217 | 0.9217 |
| 0.9220 | 0.9220 |
| 0.9226 | 0.9221 |
| 0.9217 | 0.9216 |

TABLE 11A-continued

Density (ρ, g/cm³) Calibration, Reactor 2

| ρ(Lab) | ρ(Model) |
|---|---|
| 0.9219 | 0.9222 |
| 0.9225 | 0.9224 |
| 0.9221 | 0.9223 |
| 0.9216 | 0.9217 |
| 0.9218 | 0.9219 |
| 0.9218 | 0.9213 |
| 0.9216 | 0.9220 |
| $^{v1}$0.9268 | 0.9262 |
| 0.9256 | 0.9259 |
| 0.9254 | 0.9254 |
| 0.9255 | 0.9257 |
| 0.9252 | 0.9253 |
| 0.9247 | 0.9253 |
| 0.9255 | 0.9260 |
| 0.9250 | 0.9246 |
| 0.9264 | 0.9267 |
| 0.9259 | 0.9258 |
| 0.9253 | 0.9250 |
| 0.9247 | 0.9245 |
| $^{v2}$0.9269 | 0.9270 |
| 0.9267 | 0.9268 |
| 0.9259 | 0.9263 |
| 0.9246 | 0.9249 |
| 0.9235 | 0.9235 |
| 0.9246 | 0.9250 |
| 0.9248 | 0.9246 |
| 0.9256 | 0.9257 |
| 0.9251 | 0.9253 |
| 0.9246 | 0.9246 |
| 0.9253 | 0.9253 |
| 0.9260 | 0.9259 |
| 0.9265 | 0.9268 |
| 0.9265 | 0.9264 |
| 0.9261 | 0.9260 |
| 0.9251 | 0.9256 |
| 0.9252 | 0.9254 |
| 0.9249 | 0.9254 |
| 0.9257 | 0.9255 |
| 0.9252 | 0.9247 |
| 0.9244 | 0.9249 |
| 0.9245 | 0.9245 |
| 0.9250 | 0.9248 |
| 0.9256 | 0.9260 |
| 0.9256 | 0.9260 |
| $^{v3}$0.9216 | 0.9213 |
| 0.9168 | 0.9153 |
| 0.9184 | 0.9186 |
| 0.9191 | 0.9189 |
| 0.9188 | 0.9187 |
| 0.9185 | 0.9186 |
| 0.9181 | 0.9184 |
| 0.9180 | 0.9178 |
| 0.9180 | 0.9179 |
| 0.9176 | 0.9180 |
| 0.9178 | 0.9182 |
| 0.9178 | 0.9179 |
| 0.9190 | 0.9187 |
| 0.9197 | 0.9192 |
| 0.9184 | 0.9178 |
| 0.9184 | 0.9190 |
| 0.9199 | 0.9198 |
| 0.9182 | 0.9186 |
| 0.9177 | 0.9174 |
| 0.9180 | 0.9178 |
| $^{v4}$0.9159 | 0.9161 |
| 0.9169 | 0.9169 |
| 0.9173 | 0.9177 |
| 0.9172 | 0.9176 |
| 0.9178 | 0.9181 |
| 0.9181 | 0.9187 |
| 0.9179 | 0.9174 |
| 0.9204 | 0.9204 |
| 0.9174 | 0.9180 |
| 0.9183 | 0.9185 |
| 0.9184 | 0.9180 |

TABLE 11A-continued

Density (ρ, g/cm³) Calibration, Reactor 2

| ρ(Lab) | ρ(Model) |
|---|---|
| 0.9177 | 0.9176 |
| 0.9173 | 0.9169 |
| 0.9176 | 0.9174 |
| 0.9178 | 0.9181 |
| 0.9180 | 0.9181 |
| 0.9182 | 0.9185 |

TABLE 11B

Density (ρ, g/cm³) Calibration, Reactor 2, continued

| ρ(Lab) | ρ(Model) |
|---|---|
| 0.9182 | 0.9185 |
| 0.9166 | 0.9170 |
| 0.9187 | 0.9185 |
| 0.9184 | 0.9189 |
| 0.9181 | 0.9183 |
| 0.9182 | 0.9177 |
| 0.9181 | 0.9180 |
| 0.9185 | 0.9182 |
| 0.9180 | 0.9183 |
| 0.9182 | 0.9187 |
| 0.9183 | 0.9187 |
| 0.9183 | 0.9188 |
| 0.9180 | 0.9185 |
| 0.9181 | 0.9177 |
| 0.9180 | 0.9183 |
| 0.9182 | 0.9182 |
| 0.9179 | 0.9177 |
| 0.9182 | 0.9178 |
| 0.9181 | 0.9182 |
| 0.9204 | 0.9202 |
| 0.9207 | 0.9203 |
| 0.9213 | 0.9213 |
| 0.9218 | 0.9215 |
| 0.9226 | 0.9231 |
| 0.9221 | 0.9225 |
| 0.9218 | 0.9217 |
| 0.9216 | 0.9217 |
| 0.9223 | 0.9218 |
| 0.9223 | 0.9220 |
| 0.9222 | 0.9227 |
| 0.9220 | 0.9218 |
| 0.9223 | 0.9224 |
| 0.9222 | 0.9223 |
| 0.9220 | 0.9218 |
| 0.9224 | 0.9223 |
| 0.9224 | 0.9221 |
| 0.9225 | 0.9223 |
| 0.9223 | 0.9220 |
| 0.9216 | 0.9216 |
| 0.9253 | 0.9253 |
| 0.9253 | 0.9253 |
| 0.9253 | 0.9253 |
| 0.9265 | 0.9269 |
| 0.9261 | 0.9263 |
| 0.9259 | 0.9257 |
| 0.9257 | 0.9257 |
| 0.9260 | 0.9255 |
| 0.9251 | 0.9252 |
| 0.9238 | 0.9236 |
| 0.9248 | 0.9243 |
| 0.9270 | 0.9275 |
| 0.9247 | 0.9243 |
| 0.9244 | 0.9241 |
| 0.9244 | 0.9239 |
| 0.9249 | 0.9245 |
| 0.9250 | 0.9246 |
| 0.9248 | 0.9246 |
| 0.9250 | 0.9256 |

The Raman spectra of the validation data set were also collected, and new principal component scores were calculated from the validation spectra. Using the locally-weighted regression model, the melt index of each validation sample was then calculated. The measured and predicted melt indexes are shown in Table 12. Acquisition of the validation spectra was interspersed with acquisition of the calibration spectra, at the corresponding "Vn" positions.

TABLE 12

Density (ρ, g/cm³) Validation, Reactor 2

| ρ(Lab) | ρ(Model) |
|---|---|
| V1: 0.9216 | 0.9217 |
| 0.9221 | 0.9219 |
| 0.9220 | 0.9218 |
| V2: 0.9254 | 0.9257 |
| 0.9250 | 0.9247 |
| 0.9262 | 0.9265 |
| 0.9250 | 0.9256 |
| V3: 0.9238 | 0.9243 |
| 0.9228 | 0.9230 |
| V4: 0.9182 | 0.9180 |
| 0.9184 | 0.9181 |
| 0.9185 | 0.9183 |
| 0.9185 | 0.9188 |

Figure 9B:
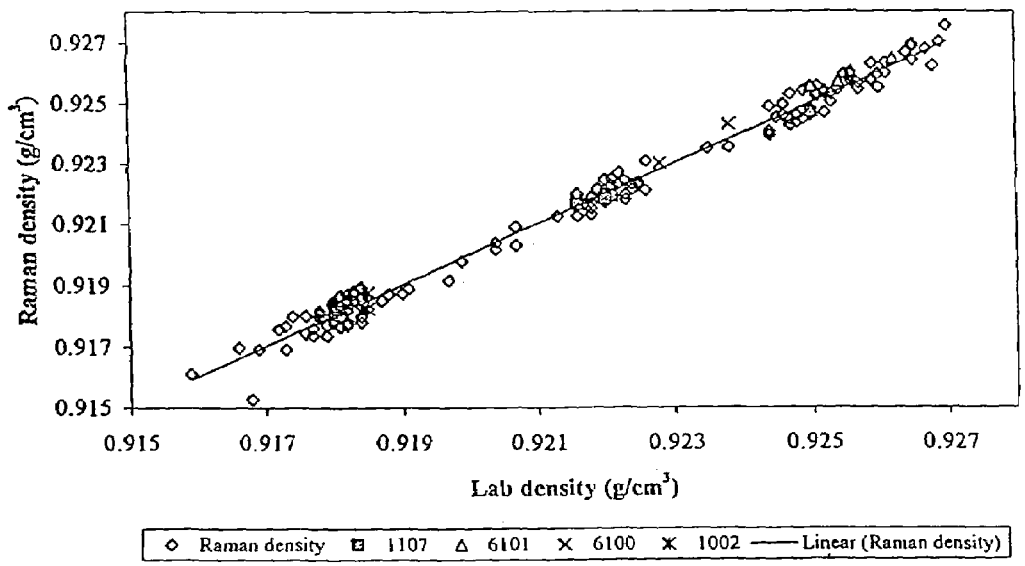

FIG. 9B depicts the data from Tables 11A, 11B and 12 graphically. The line in the Figure is the model prediction. The calculated $R^2$ value was 0.989, with a standard error of 0.00034 g/cm³.

Examples 8–9

Examples 8–9 demonstrate the effectiveness, precision and accuracy of processes of the invention to predict melt index and density on-line, in a commercial-scale fluidized-bed polymerization reactor. The Raman system was as described above but used a 400 mW diode laser operating at 785 nm. The fiber optic cable used to couple the electrical components of the instrument to the Raman probe (approximately 150 m distant) was a 62 μm excitation/100 μm collection step index silica fiber.

Melt index and density models were developed by continuously collecting, and saving Raman data as individual spectra every 3–10 minutes, on each of two reactors. Validation of each model was accomplished by then using the model on-line to determine the polymer properties.

Example 8

Polymer melt index was predicted on-line in a commercial-scale fluidized-bed reactor forming various grades of polyethylene copolymer. The prediction was carried out approximately every 12 minutes for about 5 weeks. Nearly 500 samples were also tested the laboratory, using the standard ASTM D-1238, condition E (2.16 kg load, 190° C.) protocol. The results, are shown in Table 13, where "MI model" indicates the melt index 12.16 predicted by the model, and "MI lab" indicates the value obtained in the laboratory by the ASTM method. The same data are shown graphically in FIG. 10, except that the Figure also shows the predicted MI for samples not corresponding to lab measurements. The predicted MI values are spaced sufficiently closely in time that they appear in the Figure to be a line.

TABLE 13

| Time (days) | MI model (dg/min) | MI lab (dg/min) |
|---|---|---|
| 0.009 | 0.958 | 0.957 |
| 0.086 | 1.016 | 1.020 |
| 0.155 | 1.036 | 1.030 |
| 0.258 | 1.007 | 0.998 |
| 0.327 | 1.002 | 0.996 |
| 0.404 | 0.982 | 1.006 |
| 0.499 | 0.941 | 0.927 |
| 0.585 | 0.944 | 0.940 |
| 0.654 | 1.017 | 1.015 |
| 0.748 | 1.033 | 1.037 |
| 0.826 | 0.985 | 0.989 |
| 0.903 | 0.940 | 0.970 |
| 0.998 | 0.953 | 0.930 |
| 1.084 | 0.944 | 0.950 |
| 1.161 | 0.971 | 0.980 |
| 1.204 | 1.073 | 1.060 |
| 1.247 | 1.220 | 1.210 |
| 1.290 | 1.373 | 1.360 |
| 1.324 | 1.461 | 1.460 |
| 1.367 | 1.502 | 1.520 |
| 1.419 | 1.486 | 1.506 |
| 1.995 | 2.763 | 2.770 |
| 2.081 | 2.650 | 2.650 |
| 2.159 | 2.766 | 2.810 |
| 2.236 | 2.777 | 2.590 |
| 2.339 | 2.738 | 2.740 |
| 2.399 | 2.799 | 2.800 |
| 2.511 | 2.970 | 2.971 |
| 2.546 | 3.056 | 3.072 |
| 2.580 | 3.235 | 3.226 |
| 2.666 | 3.427 | 3.423 |
| 2.752 | 3.542 | 3.545 |
| 2.838 | 3.619 | 3.699 |
| 2.907 | 3.593 | 3.580 |
| 3.001 | 3.446 | 3.380 |
| 3.079 | 3.514 | 3.500 |
| 3.165 | 3.705 | 3.710 |
| 3.242 | 3.702 | 3.710 |
| 3.337 | 3.710 | 3.710 |
| 3.397 | 3.713 | 3.710 |
| 3.509 | 3.478 | 3.482 |
| 3.578 | 3.421 | 3.361 |
| 3.664 | 3.466 | 3.465 |
| 3.750 | 3.430 | 3.443 |
| 3.836 | 3.458 | 3.459 |
| 3.913 | 3.306 | 3.300 |
| 3.999 | 3.301 | 3.290 |
| 4.042 | 3.411 | 3.220 |
| 4.085 | 3.466 | 3.460 |
| 4.171 | 3.751 | 3.730 |
| 4.248 | 3.713 | 3.700 |
| 4.334 | 3.493 | 3.500 |
| 4.403 | 3.497 | 3.460 |
| 4.498 | 3.459 | 3.406 |
| 4.584 | 3.516 | 3.528 |
| 4.670 | 3.544 | 3.555 |
| 4.747 | 3.601 | 3.616 |
| 4.833 | 3.612 | 3.593 |
| 4.902 | 3.514 | 3.536 |
| 4.997 | 3.560 | 3.559 |
| 5.091 | 3.584 | 3.677 |
| 5.177 | 3.583 | 3.350 |
| 5.255 | 3.531 | 3.554 |
| 5.332 | 3.473 | 3.476 |
| 5.409 | 3.528 | 3.521 |
| 5.504 | 3.537 | 3.526 |
| 5.581 | 3.484 | 3.436 |
| 5.667 | 3.532 | 3.592 |
| 5.753 | 3.482 | 3.516 |
| 5.839 | 3.505 | 3.516 |
| 5.900 | 3.516 | 3.464 |
| 6.003 | 3.455 | 3.464 |
| 6.080 | 3.466 | 3.394 |
| 6.166 | 3.468 | 3.439 |
| 6.252 | 3.666 | 3.655 |
| 6.330 | 3.723 | 3.714 |
| 6.407 | 3.712 | 3.778 |
| 6.510 | 3.578 | 3.555 |
| 6.588 | 3.483 | 3.480 |
| 6.665 | 3.454 | 3.470 |
| 6.751 | 3.399 | 3.540 |
| 6.854 | 3.379 | 3.360 |
| 6.906 | 1.824 | 1.810 |
| 6.949 | 1.157 | 1.140 |
| 7.000 | 0.899 | 0.860 |
| 7.043 | 0.888 | 0.883 |
| 7.086 | 0.937 | 0.940 |
| 7.129 | 1.001 | 0.980 |
| 7.164 | 1.053 | 1.060 |
| 7.250 | 1.105 | 1.110 |
| 7.336 | 1.083 | 1.070 |
| 7.413 | 1.051 | 1.040 |
| 7.508 | 1.003 | 1.010 |
| 7.585 | 0.975 | 0.973 |
| 7.680 | 0.958 | 0.950 |
| 7.749 | 0.999 | 0.960 |
| 7.835 | 1.026 | 1.000 |
| 7.903 | 1.004 | 1.000 |
| 7.998 | 1.022 | 1.033 |
| 8.101 | 1.038 | 1.037 |
| 8.161 | 1.021 | 1.025 |
| 8.265 | 0.968 | 0.990 |
| 8.325 | 0.992 | 0.988 |
| 9.460 | 0.812 | 0.754 |
| 9.503 | 0.787 | 0.790 |
| 9.546 | 0.886 | 0.871 |
| 9.580 | 0.992 | 0.989 |
| 9.666 | 0.996 | 0.991 |
| 9.752 | 1.012 | 1.020 |
| 9.830 | 1.006 | 1.020 |
| 9.899 | 1.024 | 1.010 |
| 10.002 | 1.127 | 1.110 |
| 10.088 | 1.016 | 0.990 |
| 10.165 | 1.051 | 1.030 |
| 10.243 | 1.062 | 1.080 |
| 10.329 | 1.130 | 1.130 |
| 10.397 | 1.052 | 1.010 |
| 10.501 | 1.057 | 1.040 |
| 10.578 | 1.131 | 1.130 |
| 10.664 | 1.130 | 1.140 |
| 10.750 | 1.141 | 1.100 |
| 10.836 | 1.099 | 1.130 |
| 10.905 | 1.121 | 1.140 |
| 10.999 | 1.057 | 1.000 |
| 11.042 | 1.107 | 1.085 |
| 11.085 | 1.314 | 1.302 |
| 11.120 | 1.451 | 1.426 |
| 11.163 | 1.497 | 1.495 |
| 11.249 | 1.444 | 1.458 |
| 11.326 | 1.374 | 1.255 |
| 11.395 | 1.462 | 1.468 |
| 11.507 | 1.412 | 1.340 |
| 11.584 | 1.385 | 1.400 |
| 11.670 | 1.364 | 1.370 |
| 11.748 | 1.332 | 1.330 |
| 11.834 | 1.370 | 1.370 |
| 11.868 | 1.675 | 1.680 |
| 11.911 | 2.443 | 2.431 |
| 11.963 | 3.017 | 3.029 |
| 11.997 | 3.102 | 3.107 |
| 12.040 | 3.207 | 3.201 |
| 12.083 | 3.357 | 3.350 |
| 12.126 | 3.323 | 3.248 |
| 12.169 | 3.330 | 3.333 |
| 12.246 | 3.505 | 3.482 |
| 12.332 | 3.491 | 3.211 |
| 12.401 | 3.691 | 3.691 |
| 12.504 | 3.713 | 3.660 |
| 12.582 | 4.040 | 4.080 |
| 12.668 | 3.947 | 3.960 |
| 12.754 | 3.775 | 3.770 |
| 12.805 | 3.743 | 3.730 |

TABLE 13-continued

| Time (days) | MI model (dg/min) | MI lab (dg/min) |
|---|---|---|
| 12.840 | 3.698 | 3.600 |
| 12.900 | 3.753 | 3.770 |
| 12.960 | 3.964 | 3.950 |
| 13.003 | 3.693 | 3.150 |
| 13.029 | 3.501 | 3.510 |
| 13.081 | 3.112 | 3.110 |
| 13.132 | 3.063 | 2.870 |
| 13.167 | 3.523 | 3.520 |
| 13.210 | 3.624 | 3.630 |
| 13.253 | 3.580 | 3.600 |
| 13.296 | 3.706 | 3.720 |
| 13.330 | 3.700 | 3.700 |
| 13.459 | 3.222 | 3.220 |
| 13.502 | 3.188 | 3.180 |
| 13.545 | 3.234 | 3.240 |
| 13.579 | 3.256 | 3.250 |
| 13.622 | 3.313 | 3.290 |
| 13.674 | 3.327 | 3.350 |
| 13.751 | 3.404 | 3.350 |
| 13.837 | 3.488 | 3.550 |
| 13.898 | 3.421 | 3.390 |
| 14.001 | 3.425 | 3.440 |
| 14.087 | 3.487 | 3.500 |
| 14.164 | 3.459 | 3.480 |
| 14.250 | 3.429 | 3.420 |
| 14.345 | 3.373 | 3.380 |
| 14.396 | 3.363 | 3.370 |
| 14.500 | 3.420 | 3.259 |
| 14.586 | 3.467 | 3.462 |
| 14.663 | 3.566 | 3.400 |
| 14.749 | 3.478 | 3.475 |
| 14.826 | 3.383 | 3.409 |
| 14.904 | 3.323 | 3.341 |
| 14.998 | 3.636 | 3.640 |
| 15.084 | 3.537 | 3.550 |
| 15.170 | 3.369 | 3.360 |
| 15.256 | 3.270 | 3.300 |
| 15.334 | 3.644 | 3.630 |
| 15.394 | 3.289 | 3.310 |
| 15.497 | 3.136 | 3.150 |
| 15.583 | 3.439 | 3.435 |
| 15.661 | 3.460 | 3.448 |
| 15.755 | 3.461 | 3.494 |
| 15.833 | 3.466 | 3.447 |
| 15.901 | 3.612 | 3.620 |
| 16.005 | 3.458 | 3.450 |
| 16.039 | 3.301 | 3.310 |
| 16.082 | 3.222 | 3.220 |
| 16.125 | 2.997 | 2.980 |
| 16.168 | 2.804 | 2.790 |
| 16.211 | 2.751 | 2.740 |
| 16.254 | 2.372 | 2.390 |
| 16.288 | 2.360 | 2.360 |
| 16.331 | 2.387 | 2.400 |
| 16.400 | 2.467 | 2.350 |
| 16.495 | 2.569 | 2.564 |
| 16.581 | 2.609 | 2.610 |
| 16.667 | 2.680 | 2.660 |
| 16.710 | 2.649 | 2.638 |
| 16.744 | 2.074 | 2.079 |
| 16.796 | 1.916 | 1.938 |
| 16.830 | 1.917 | 1.995 |
| 16.865 | 1.960 | 1.967 |
| 16.899 | 2.049 | 2.070 |
| 16.994 | 2.211 | 2.200 |
| 17.080 | 2.152 | 2.150 |
| 17.166 | 2.322 | 2.320 |
| 17.252 | 2.352 | 2.240 |
| 17.329 | 2.342 | 2.340 |
| 17.398 | 2.239 | 2.247 |
| 17.501 | 2.110 | 2.112 |
| 17.587 | 2.081 | 2.080 |
| 17.664 | 2.098 | 2.119 |
| 17.750 | 2.147 | 2.130 |
| 17.836 | 2.273 | 2.301 |
| 17.905 | 2.202 | 2.205 |
| 18.000 | 2.058 | 2.050 |
| 18.086 | 2.002 | 2.080 |
| 18.163 | 2.043 | 2.040 |
| 18.249 | 2.094 | 2.110 |
| 18.335 | 2.203 | 2.180 |
| 18.395 | 2.260 | 2.250 |
| 18.490 | 2.264 | 2.257 |
| 18.662 | 2.292 | 2.277 |
| 18.757 | 2.195 | 2.158 |
| 18.843 | 2.208 | 2.189 |
| 18.903 | 2.112 | 2.139 |
| 18.963 | 1.676 | 1.690 |
| 18.997 | 1.390 | 1.400 |
| 19.040 | 1.219 | 1.240 |
| 19.083 | 1.103 | 1.080 |
| 19.126 | 1.125 | 1.080 |
| 19.169 | 1.077 | 1.100 |
| 19.255 | 1.030 | 1.060 |
| 19.341 | 1.019 | 1.010 |
| 19.393 | 0.997 | 1.050 |
| 19.505 | 0.926 | 0.927 |
| 19.539 | 0.875 | 0.886 |
| 19.582 | 0.605 | 0.604 |
| 19.617 | 0.563 | 0.542 |
| 19.660 | 0.482 | 0.502 |
| 19.746 | 0.550 | 0.551 |
| 19.832 | 0.575 | 0.581 |
| 19.900 | 0.562 | 0.545 |
| 19.995 | 0.541 | 0.539 |
| 20.090 | 0.568 | 0.574 |
| 20.167 | 0.593 | 0.572 |
| 20.253 | 0.620 | 0.585 |
| 20.330 | 0.526 | 0.530 |
| 20.399 | 0.500 | 0.506 |
| 20.511 | 0.557 | 0.529 |
| 20.580 | 0.506 | 0.511 |
| 20.657 | 0.538 | 0.526 |
| 20.752 | 0.533 | 0.526 |
| 20.838 | 0.516 | 0.516 |
| 20.898 | 0.531 | 0.536 |
| 21.000 | 0.509 | 0.543 |
| 21.095 | 0.523 | 0.522 |
| 21.163 | 0.594 | 0.542 |
| 21.249 | 0.479 | 0.530 |
| 21.327 | 0.515 | 0.520 |
| 21.404 | 0.960 | 0.920 |
| 21.456 | 1.040 | 1.056 |
| 21.499 | 1.156 | 1.133 |
| 21.542 | 1.152 | 1.172 |
| 21.585 | 1.157 | 1.080 |
| 21.671 | 1.005 | 1.124 |
| 21.748 | 1.090 | 1.067 |
| 21.834 | 1.060 | 1.036 |
| 21.894 | 1.090 | 1.091 |
| 21.998 | 1.060 | 1.110 |
| 22.041 | 1.209 | 1.230 |
| 22.084 | 1.548 | 1.650 |
| 22.135 | 2.062 | 2.110 |
| 22.170 | 2.106 | 2.110 |
| 22.221 | 2.066 | 2.120 |
| 22.247 | 2.108 | 2.050 |
| 22.324 | 2.117 | 2.080 |
| 22.402 | 2.155 | 2.320 |
| 22.496 | 2.156 | 2.190 |
| 22.582 | 2.013 | 2.040 |
| 22.660 | 2.067 | 2.080 |
| 22.754 | 2.108 | 2.100 |
| 22.823 | 2.108 | 2.120 |
| 22.858 | 2.348 | 2.350 |
| 22.901 | 3.418 | 3.380 |
| 22.961 | 3.794 | 4.122 |
| 23.004 | 3.507 | 3.588 |
| 23.038 | 3.358 | 3.316 |
| 23.081 | 3.234 | 3.192 |
| 23.133 | 3.187 | 3.196 |
| 23.167 | 3.424 | 3.417 |

TABLE 13-continued

| Time (days) | MI model (dg/min) | MI lab (dg/min) |
|---|---|---|
| 23.253 | 3.507 | 3.497 |
| 23.331 | 3.587 | 3.581 |
| 23.408 | 3.353 | 3.351 |
| 23.503 | 3.292 | 3.300 |
| 23.580 | 3.344 | 3.330 |
| 23.666 | 3.395 | 3.380 |
| 23.752 | 3.396 | 3.390 |
| 23.838 | 3.406 | 3.270 |
| 23.898 | 3.386 | 3.390 |
| 23.993 | 3.509 | 3.478 |
| 24.079 | 3.576 | 3.586 |
| 24.165 | 3.530 | 3.401 |
| 24.242 | 3.513 | 3.520 |
| 24.320 | 3.417 | 3.414 |
| 24.397 | 3.463 | 3.439 |
| 24.500 | 3.406 | 3.410 |
| 24.586 | 3.399 | 3.400 |
| 24.664 | 3.241 | 3.290 |
| 24.750 | 3.272 | 3.280 |
| 24.836 | 3.322 | 3.280 |
| 24.896 | 3.480 | 3.481 |
| 24.999 | 3.345 | 3.313 |
| 25.076 | 3.316 | 3.308 |
| 25.162 | 3.479 | 3.479 |
| 25.240 | 3.491 | 3.509 |
| 25.343 | 3.544 | 3.525 |
| 25.395 | 3.373 | 3.405 |
| 25.498 | 3.582 | 3.580 |
| 25.584 | 3.371 | 3.370 |
| 25.670 | 3.223 | 3.190 |
| 25.747 | 3.274 | 3.300 |
| 25.833 | 3.518 | 3.500 |
| 25.919 | 3.414 | 3.409 |
| 25.997 | 3.445 | 3.451 |
| 26.074 | 3.460 | 3.488 |
| 26.169 | 3.591 | 3.603 |
| 26.246 | 3.825 | 3.836 |
| 26.332 | 3.681 | 3.668 |
| 26.401 | 3.392 | 3.372 |
| 26.487 | 3.395 | 3.380 |
| 26.573 | 3.404 | 3.390 |
| 26.667 | 3.320 | 3.300 |
| 26.753 | 3.370 | 3.370 |
| 26.831 | 3.428 | 3.410 |
| 26.900 | 3.539 | 3.280 |
| 27.003 | 3.731 | 3.723 |
| 27.080 | 3.498 | 3.476 |
| 27.158 | 3.572 | 3.552 |
| 27.252 | 3.349 | 3.361 |
| 27.287 | 2.622 | 3.265 |
| 27.330 | 2.483 | 2.481 |
| 27.381 | 2.497 | 2.505 |
| 27.407 | 2.433 | 2.438 |
| 27.467 | 2.140 | 2.170 |
| 27.510 | 2.047 | 2.050 |
| 27.536 | 1.920 | 1.920 |
| 27.579 | 1.883 | 1.880 |
| 27.665 | 2.051 | 2.030 |
| 27.751 | 2.052 | 2.060 |
| 27.837 | 2.108 | 2.090 |
| 27.906 | 2.066 | 2.060 |
| 28.009 | 2.153 | 2.150 |
| 28.086 | 2.136 | 2.140 |
| 28.164 | 2.096 | 1.135 |
| 28.241 | 2.125 | 2.140 |
| 28.293 | 1.861 | 1.860 |
| 28.336 | 1.483 | 1.490 |
| 28.362 | 1.473 | 1.620 |
| 28.405 | 1.472 | 1.470 |
| 28.465 | 1.482 | 1.500 |
| 28.508 | 1.486 | 1.470 |
| 28.542 | 1.332 | 1.320 |
| 28.585 | 1.375 | 1.370 |
| 28.671 | 1.427 | 1.440 |
| 28.749 | 1.404 | 1.410 |
| 28.835 | 1.313 | 1.310 |
| 28.903 | 1.380 | 1.380 |
| 28.998 | 1.331 | 1.340 |
| 29.084 | 1.367 | 1.360 |
| 29.170 | 1.307 | 1.320 |
| 29.247 | 1.319 | 1.320 |
| 29.333 | 1.374 | 1.370 |
| 29.394 | 1.261 | 1.250 |
| 29.505 | 1.216 | 1.220 |
| 29.574 | 1.229 | 1.220 |
| 29.669 | 1.227 | 1.230 |
| 29.755 | 1.215 | 1.230 |
| 29.832 | 1.206 | 1.210 |
| 29.901 | 1.222 | 1.220 |
| 29.987 | 1.205 | 1.210 |
| 30.082 | 1.347 | 1.350 |
| 30.125 | 1.221 | 1.240 |
| 30.168 | 1.177 | 1.180 |
| 30.211 | 1.063 | 1.080 |
| 30.254 | 1.047 | 1.010 |
| 30.322 | 1.057 | 1.070 |
| 30.400 | 1.012 | 1.020 |
| 30.503 | 0.987 | 1.012 |
| 30.580 | 0.943 | 0.932 |
| 30.666 | 0.889 | 0.902 |
| 31.707 | 1.260 | 1.248 |
| 31.750 | 2.776 | 2.763 |
| 31.784 | 3.394 | 3.411 |
| 31.836 | 3.950 | 3.967 |
| 31.879 | 4.110 | 4.098 |
| 31.905 | 3.968 | 3.969 |
| 31.956 | 4.140 | 4.110 |
| 32.017 | 4.019 | 4.040 |
| 32.085 | 4.431 | 4.440 |
| 32.171 | 4.645 | 4.650 |
| 32.249 | 4.737 | 4.730 |
| 32.326 | 4.827 | 4.840 |
| 32.404 | 4.756 | 4.754 |
| 32.498 | 4.212 | 4.182 |
| 32.576 | 3.953 | 3.975 |
| 32.627 | 4.189 | 4.217 |
| 32.670 | 4.309 | 4.297 |
| 32.748 | 4.328 | 4.320 |
| 32.825 | 4.300 | 4.315 |
| 32.902 | 4.338 | 4.366 |
| 32.997 | 4.263 | 4.270 |
| 33.049 | 4.225 | 4.230 |
| 33.083 | 3.947 | 3.930 |
| 33.126 | 3.605 | 3.610 |
| 33.169 | 3.446 | 3.460 |
| 33.212 | 3.416 | 3.400 |
| 33.246 | 3.511 | 3.530 |
| 33.332 | 3.503 | 3.520 |
| 33.401 | 3.387 | 3.380 |
| 33.496 | 3.327 | 3.340 |
| 33.590 | 3.303 | 3.292 |
| 33.668 | 3.472 | 3.457 |
| 33.754 | 3.625 | 3.595 |
| 33.831 | 3.544 | 3.520 |
| 33.900 | 3.603 | 3.626 |
| 33.986 | 3.551 | 3.570 |
| 34.081 | 3.618 | 3.610 |
| 34.158 | 3.478 | 3.470 |
| 34.253 | 3.572 | 3.580 |
| 34.321 | 3.576 | 3.560 |
| 34.399 | 3.663 | 3.660 |
| 34.493 | 3.596 | 3.609 |
| 34.588 | 3.312 | 3.331 |
| 34.665 | 3.238 | 3.261 |
| 34.751 | 3.358 | 3.362 |
| 34.820 | 3.424 | 3.416 |
| 34.906 | 3.465 | 3.458 |
| 35.009 | 3.444 | 3.440 |
| 35.087 | 3.450 | 3.470 |
| 35.164 | 3.474 | 3.470 |
| 35.250 | 3.485 | 3.510 |
| 35.328 | 3.627 | 3.630 |

TABLE 13-continued

| Time (days) | MI model (dg/min) | MI lab (dg/min) |
|---|---|---|
| 35.396 | 3.618 | 3.620 |
| 35.500 | 3.654 | 3.669 |
| 35.586 | 3.354 | 3.311 |
| 35.663 | 3.389 | 3.404 |
| 35.749 | 3.463 | 3.452 |
| 35.835 | 3.550 | 3.544 |
| 35.895 | 3.449 | 3.484 |
| 36.007 | 3.371 | 3.380 |
| 36.084 | 3.382 | 3.390 |
| 36.170 | 3.448 | 3.440 |
| 36.248 | 3.634 | 3.630 |
| 36.334 | 3.743 | 3.730 |
| 36.403 | 3.633 | 3.630 |
| 36.506 | 3.376 | 3.382 |
| 36.583 | 3.399 | 3.398 |
| 36.669 | 3.300 | 3.314 |
| 36.747 | 1.486 | 1.483 |
| 36.781 | 1.435 | 1.429 |
| 36.815 | 1.283 | 1.296 |
| 36.858 | 1.293 | 1.306 |
| 36.919 | 1.394 | 1.390 |
| 36.962 | 1.404 | 1.420 |
| 37.048 | 1.417 | 1.430 |
| 37.125 | 1.457 | 1.480 |
| 37.220 | 1.551 | 1.570 |
| 37.288 | 1.571 | 1.570 |
| 37.366 | 1.571 | 1.540 |

Figure 10:
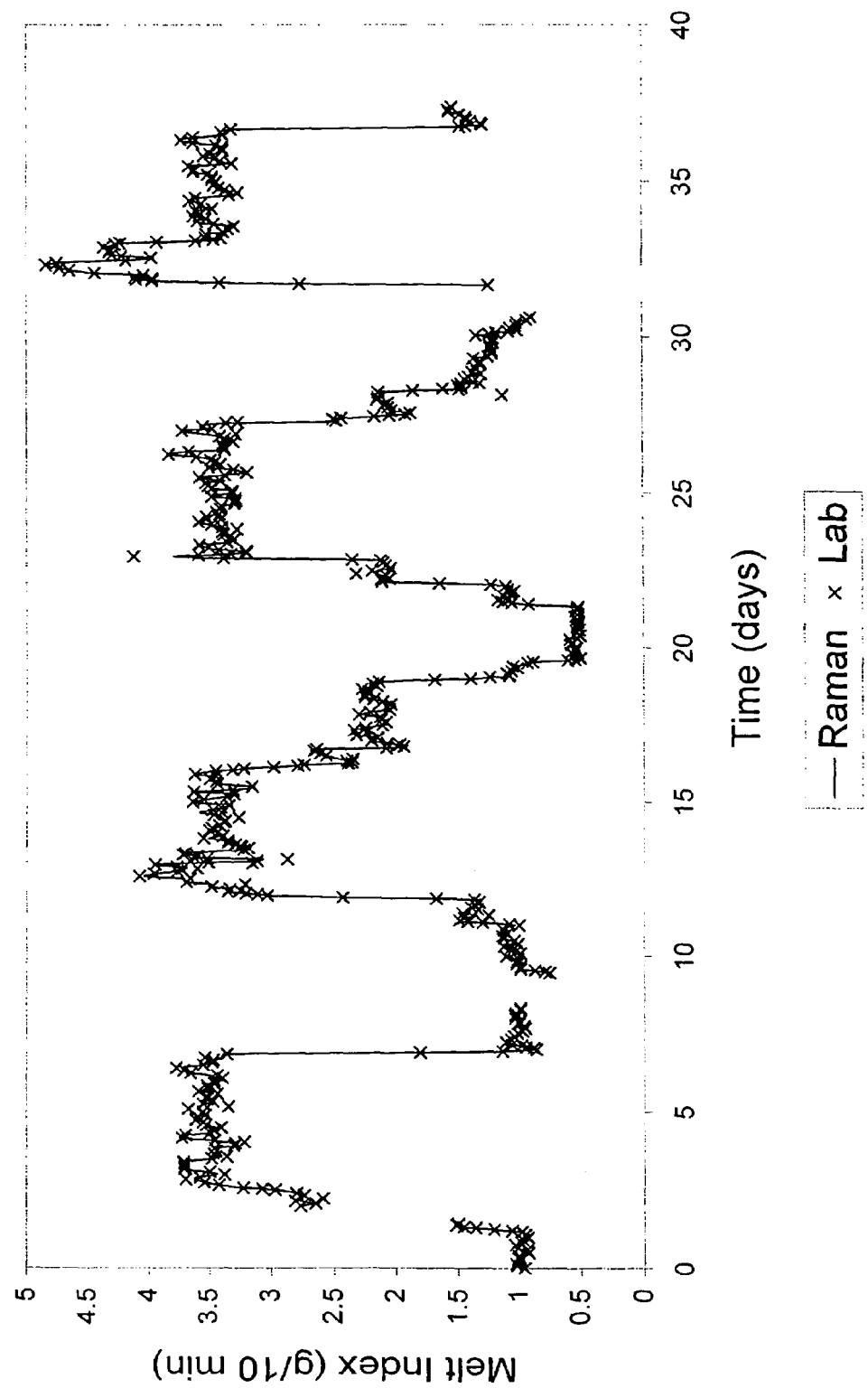
FIG. 10 shows predicted versus measured melt indices from on-line Raman analyses in a commercial-scale fluidized-bed reactor, over a period of about five weeks.

Table 13 and FIG. 10 show the accuracy and precision of the on-line process over a long period of time, and a range of melt index values. The gaps in the Figure indicate periods when the reactor was down. The horizontal regions indicate continued production of a particular grade, and the steep vertical regions correspond to transitions between different grades. The data further show that the inventive on-line processes are accurate and precise even during grade transitions. The 3σ accuracy of the predictions relative to the lab values over the entire 5-week period was ±0.069 g/10 min.

Additionally, to test for model precision and long-term drift, the predicted MI of approximately 2200 samples of a particular grade was monitored for a static sample over a four-week period, in each of two commercial-scale fluidized bed reactors. In each reactor, the data showed a 3σ standard deviation of 0.012 g/10 min (for sample with melt indexes of 1.0 and 0.98 g/10 min; i.e., about 1%), and no measurable long-term drift.

Example 9

Polymer density was predicted on-line along with the melt index predictions of Example 8, applying a density model to the same samples and spectra as in Example 8. Nearly 300 samples were also tested the laboratory, using the standard ASTM D1505 and ASTM D1928, procedure C protocol. The results, are shown in Table 14, where "ρ model" indicates the density predicted by the model, and "ρ lab" indicates the value obtained in the laboratory by the ASTM method. The same data are shown graphically in FIG. 11, except that the Figure also shows the predicted density for samples not corresponding to lab measurements. The predicted density values are spaced sufficiently closely in time that they appear in the Figure to be a line.

TABLE 14

| Time (days) | ρ model (g/cm³) | ρ lab (g/cm³) |
|---|---|---|
| 0.009 | 0.9173 | 0.9173 |
| 0.155 | 0.9183 | 0.9182 |
| 0.327 | 0.9176 | 0.9175 |
| 0.499 | 0.9175 | 0.9175 |
| 0.654 | 0.9172 | 0.9173 |
| 0.826 | 0.9178 | 0.9178 |
| 0.998 | 0.9173 | 0.9173 |
| 1.161 | 0.9173 | 0.9173 |
| 1.247 | 0.9167 | 0.9166 |
| 1.324 | 0.9169 | 0.9169 |
| 1.995 | 0.9172 | 0.9172 |
| 2.159 | 0.9168 | 0.9168 |
| 2.339 | 0.9169 | 0.9168 |
| 2.511 | 0.9187 | 0.9186 |
| 2.580 | 0.9185 | 0.9184 |
| 2.666 | 0.9183 | 0.9184 |
| 2.838 | 0.9179 | 0.9180 |
| 3.001 | 0.9166 | 0.9167 |
| 3.165 | 0.9173 | 0.9173 |
| 3.337 | 0.9172 | 0.9172 |
| 3.509 | 0.9181 | 0.9181 |
| 3.664 | 0.9173 | 0.9173 |
| 3.836 | 0.9173 | 0.9172 |
| 3.999 | 0.9165 | 0.9165 |
| 4.171 | 0.9176 | 0.9177 |
| 4.334 | 0.9175 | 0.9173 |
| 4.498 | 0.9171 | 0.9172 |
| 4.670 | 0.9177 | 0.9175 |
| 4.833 | 0.9179 | 0.9179 |
| 4.997 | 0.9179 | 0.9178 |
| 5.177 | 0.9175 | 0.9176 |
| 5.332 | 0.9172 | 0.9173 |
| 5.504 | 0.9177 | 0.9177 |
| 5.667 | 0.9173 | 0.9173 |
| 5.839 | 0.9171 | 0.9171 |
| 6.003 | 0.9166 | 0.9166 |
| 6.166 | 0.9169 | 0.9169 |
| 6.330 | 0.9179 | 0.9180 |
| 6.510 | 0.9175 | 0.9175 |
| 6.665 | 0.9177 | 0.9177 |
| 6.854 | 0.9171 | 0.9170 |
| 6.949 | 0.9157 | 0.9157 |
| 7.000 | 0.9165 | 0.9165 |
| 7.086 | 0.9167 | 0.9167 |
| 7.164 | 0.9174 | 0.9174 |
| 7.336 | 0.9179 | 0.9180 |
| 7.508 | 0.9182 | 0.9181 |
| 7.680 | 0.9179 | 0.9178 |
| 7.835 | 0.9178 | 0.9178 |
| 7.998 | 0.9175 | 0.9176 |
| 8.161 | 0.9173 | 0.9174 |
| 8.325 | 0.9168 | 0.9169 |
| 9.503 | 0.9188 | 0.9190 |
| 9.580 | 0.9185 | 0.9185 |
| 9.666 | 0.9179 | 0.9181 |
| 9.752 | 0.9175 | 0.9174 |
| 9.830 | 0.9175 | 0.9174 |
| 10.002 | 0.9173 | 0.9174 |
| 10.165 | 0.9173 | 0.9171 |
| 10.329 | 0.9172 | 0.9173 |
| 10.501 | 0.9172 | 0.9173 |
| 10.664 | 0.9170 | 0.917 |
| 10.836 | 0.9171 | 0.9171 |
| 10.999 | 0.9186 | 0.9186 |
| 11.085 | 0.9175 | 0.9175 |
| 11.163 | 0.9177 | 0.9177 |
| 11.249 | 0.9179 | 0.9179 |
| 11.326 | 0.9184 | 0.9183 |
| 11.507 | 0.9176 | 0.9177 |
| 11.670 | 0.9175 | 0.9173 |
| 11.834 | 0.9173 | 0.9172 |
| 11.911 | 0.9176 | 0.9175 |
| 11.997 | 0.9173 | 0.9173 |
| 12.083 | 0.9180 | 0.9182 |
| 12.169 | 0.9181 | 0.9182 |
| 12.332 | 0.9186 | 0.9185 |

TABLE 14-continued

| Time (days) | ρ model (g/cm³) | ρ lab (g/cm³) |
|---|---|---|
| 12.504 | 0.9172 | 0.9172 |
| 12.668 | 0.9167 | 0.9166 |
| 12.840 | 0.9165 | 0.9166 |
| 13.003 | 0.9173 | 0.9173 |
| 13.167 | 0.9176 | 0.9176 |
| 13.330 | 0.9176 | 0.9175 |
| 13.502 | 0.9174 | 0.9172 |
| 13.674 | 0.9173 | 0.9174 |
| 13.837 | 0.9176 | 0.9176 |
| 14.001 | 0.9176 | 0.9175 |
| 14.164 | 0.9174 | 0.9175 |
| 14.345 | 0.9172 | 0.9170 |
| 14.500 | 0.9173 | 0.9173 |
| 14.663 | 0.9178 | 0.9179 |
| 14.826 | 0.9185 | 0.9183 |
| 14.998 | 0.9174 | 0.9173 |
| 15.170 | 0.9172 | 0.9171 |
| 15.334 | 0.9171 | 0.9171 |
| 15.497 | 0.9174 | 0.9173 |
| 15.661 | 0.9170 | 0.9171 |
| 15.833 | 0.9171 | 0.9171 |
| 16.005 | 0.9174 | 0.9175 |
| 16.082 | 0.9171 | 0.9172 |
| 16.168 | 0.9176 | 0.9175 |
| 16.254 | 0.9181 | 0.9181 |
| 16.331 | 0.9180 | 0.9179 |
| 16.495 | 0.9171 | 0.9171 |
| 16.667 | 0.9171 | 0.9169 |
| 16.744 | 0.9171 | 0.9169 |
| 16.830 | 0.9163 | 0.9163 |
| 16.994 | 0.9164 | 0.9164 |
| 17.166 | 0.9165 | 0.9163 |
| 17.329 | 0.9162 | 0.9161 |
| 17.501 | 0.9164 | 0.9164 |
| 17.664 | 0.9169 | 0.9169 |
| 17.836 | 0.9165 | 0.9167 |
| 18.000 | 0.9175 | 0.9173 |
| 18.163 | 0.9168 | 0.9168 |
| 18.335 | 0.9170 | 0.9171 |
| 18.490 | 0.9168 | 0.9168 |
| 18.662 | 0.9176 | 0.9176 |
| 18.843 | 0.9172 | 0.9171 |
| 18.997 | 0.9181 | 0.9181 |
| 19.083 | 0.9176 | 0.9174 |
| 19.169 | 0.9163 | 0.9164 |
| 19.341 | 0.9163 | 0.9163 |
| 19.505 | 0.9168 | 0.9168 |
| 19.582 | 0.9199 | 0.9199 |
| 19.660 | 0.9214 | 0.9214 |
| 19.746 | 0.9202 | 0.9204 |
| 19.832 | 0.9199 | 0.9200 |
| 19.995 | 0.9206 | 0.9206 |
| 20.167 | 0.9208 | 0.9207 |
| 20.330 | 0.9208 | 0.9206 |
| 20.511 | 0.9207 | 0.9207 |
| 20.657 | 0.9203 | 0.9203 |
| 20.838 | 0.9215 | 0.9214 |
| 21.000 | 0.9206 | 0.9205 |
| 21.163 | 0.9208 | 0.9207 |
| 21.327 | 0.9211 | 0.9210 |
| 21.404 | 0.9186 | 0.9188 |
| 21.499 | 0.9170 | 0.9168 |
| 21.585 | 0.9168 | 0.9167 |
| 21.671 | 0.9172 | 0.9172 |
| 21.834 | 0.9170 | 0.9170 |
| 21.998 | 0.9171 | 0.9171 |
| 22.084 | 0.9174 | 0.9174 |
| 22.170 | 0.9164 | 0.9164 |
| 22.247 | 0.9167 | 0.9167 |
| 22.324 | 0.9168 | 0.9167 |
| 22.496 | 0.9176 | 0.9177 |
| 22.660 | 0.9166 | 0.9167 |
| 22.823 | 0.9168 | 0.9168 |
| 22.901 | 0.9169 | 0.9168 |
| 23.004 | 0.9175 | 0.9175 |
| 23.167 | 0.9184 | 0.9184 |
| 23.331 | 0.9180 | 0.9178 |
| 23.503 | 0.9177 | 0.9178 |
| 23.666 | 0.9175 | 0.9175 |
| 23.838 | 0.9174 | 0.9175 |
| 23.993 | 0.9182 | 0.9183 |
| 24.365 | 0.9184 | 0.9184 |
| 24.320 | 0.9172 | 0.9172 |
| 24.500 | 0.9175 | 0.9173 |
| 24.664 | 0.9178 | 0.9178 |
| 24.836 | 0.9185 | 0.9184 |
| 24.999 | 0.9180 | 0.9181 |
| 25.162 | 0.9172 | 0.9172 |
| 25.343 | 0.9176 | 0.9175 |
| 25.498 | 0.9169 | 0.9170 |
| 25.670 | 0.9173 | 0.9173 |
| 25.833 | 0.9171 | 0.9171 |
| 25.997 | 0.9172 | 0.9172 |
| 26.169 | 0.9173 | 0.9173 |
| 26.332 | 0.9172 | 0.9172 |
| 26.487 | 0.9172 | 0.9173 |
| 26.667 | 0.9173 | 0.9174 |
| 26.831 | 0.9173 | 0.9173 |
| 27.003 | 0.9174 | 0.9174 |
| 27.158 | 0.9164 | 0.9164 |
| 27.330 | 0.9173 | 0.9174 |
| 27.407 | 0.9162 | 0.9162 |
| 27.510 | 0.9162 | 0.9160 |
| 27.579 | 0.9169 | 0.9169 |
| 27.665 | 0.9169 | 0.9168 |
| 27.837 | 0.9169 | 0.9168 |
| 28.009 | 0.9169 | 0.9171 |
| 28.164 | 0.9168 | 0.9169 |
| 28.241 | 0.9174 | 0.9173 |
| 28.336 | 0.9167 | 0.9168 |
| 28.405 | 0.9161 | 0.9160 |
| 28.508 | 0.9164 | 0.9164 |
| 28.671 | 0.9169 | 0.9168 |
| 28.835 | 0.9168 | 0.9168 |
| 28.998 | 0.9164 | 0.9164 |
| 29.170 | 0.9167 | 0.9163 |
| 29.333 | 0.9169 | 0.9170 |
| 29.505 | 0.9164 | 0.9163 |
| 29.669 | 0.9171 | 0.9170 |
| 29.832 | 0.9173 | 0.9173 |
| 29.987 | 0.9174 | 0.9177 |
| 30.168 | 0.9165 | 0.9164 |
| 30.254 | 0.9172 | 0.9172 |
| 30.322 | 0.9170 | 0.9171 |
| 30.400 | 0.9162 | 0.9162 |
| 30.503 | 0.9171 | 0.9173 |
| 30.666 | 0.9181 | 0.9180 |
| 31.750 | 0.9205 | 0.9205 |
| 31.836 | 0.9195 | 0.9195 |
| 31.905 | 0.9189 | 0.9188 |
| 32.017 | 0.9174 | 0.9176 |
| 32.171 | 0.9176 | 0.9177 |
| 32.326 | 0.9176 | 0.9175 |
| 32.498 | 0.9161 | 0.9160 |
| 32.670 | 0.9171 | 0.9171 |
| 32.825 | 0.9175 | 0.9174 |
| 32.997 | 0.9171 | 0.9171 |
| 33.083 | 0.9170 | 0.9169 |
| 33.169 | 0.9171 | 0.9170 |
| 33.246 | 0.9170 | 0.9170 |
| 33.332 | 0.9170 | 0.9170 |
| 33.496 | 0.9175 | 0.9175 |
| 33.668 | 0.9174 | 0.9176 |
| 33.831 | 0.9168 | 0.9170 |
| 33.986 | 0.9169 | 0.9168 |
| 34.158 | 0.9171 | 0.9170 |
| 34.321 | 0.9174 | 0.9175 |
| 34.493 | 0.9169 | 0.9170 |
| 34.665 | 0.9170 | 0.9170 |
| 34.820 | 0.9172 | 0.9171 |
| 35.009 | 0.9172 | 0.9173 |
| 35.164 | 0.9176 | 0.9176 |

TABLE 14-continued

| Time (days) | ρ model (g/cm³) | ρ lab (g/cm³) |
|---|---|---|
| 35.328 | 0.9177 | 0.9176 |
| 35.500 | 0.9176 | 0.9176 |
| 35.663 | 0.9183 | 0.9182 |
| 35.835 | 0.9169 | 0.9168 |
| 36.007 | 0.9166 | 0.9164 |
| 36.170 | 0.9174 | 0.9174 |
| 36.334 | 0.9169 | 0.9171 |
| 36.506 | 0.9172 | 0.9173 |
| 36.669 | 0.9169 | 0.9169 |
| 36.747 | 0.9162 | 0.9162 |
| 36.815 | 0.9162 | 0.9162 |
| 36.962 | 0.9172 | 0.9172 |
| 37.125 | 0.9174 | 0.9172 |
| 37.220 | 0.9175 | 0.9174 |

Figure 11:
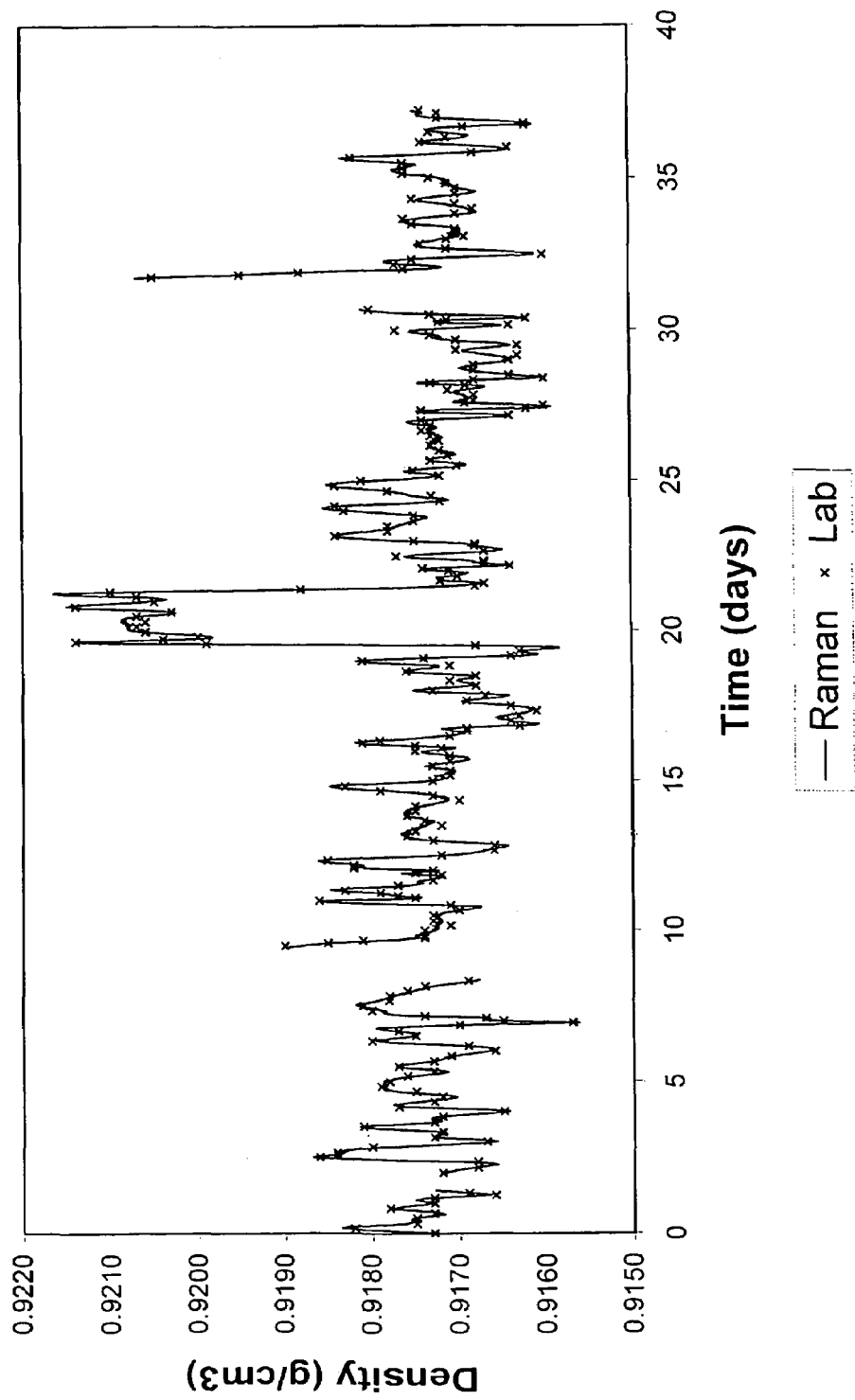
FIG. 11 shows predicted versus measured densities from on-line Raman analyses in a commercial-scale fluidized-bed reactor, over a period of about five weeks.

Table 14 and FIG. 11 show the accuracy and precision of the on-line process over a long period of time, and a range of density values. As in the previous Example, the gaps in the Figure indicate periods when the reactor was down, the horizontal regions indicate continued production of a particular grade, and the steep vertical regions correspond to transitions between different grades. The data further show that the inventive on-line processes are accurate and precise even during grade transitions. The 3σ accuracy of the predictions relative to the lab values over the entire 5-week period was ±0.00063 g/cm³.

Additionally, to test for model precision and long-term drift, the predicted density of the same approximately 2200 samples of Example 8 was monitored for a static sample over a four-week period, in each of two commercial-scale fluidized bed reactors. In each reactor, the data showed a 3σ standard deviation of 0.00006 g/cm³ (for samples with densities of 0.9177 and 0.9178 g/cm³), and no measurable long-term drift.

Various tradenames used herein are indicated by a ™ symbol, indicating that the names may be protected by certain trademark rights. Some such names may also be registered trademarks in various jurisdictions.

All patents, test procedures, and other documents cited herein, including priority document U.S. Provisional Application No. 60/345337, are fully incorporated by reference to the extent such disclosure is not inconsistent with this invention and for all jurisdictions in which such incorporation is permitted.

What is claimed is:

1. A process for determining polymer properties in a polymerization reactor system, the process comprising:
   (a) obtaining a regression model for determining a polymer property, the regression model including principal component loadings and principal component scores;
   (b) acquiring a Raman spectrum of a sample comprising polyolefin;
   (c) calculating a new principal component score from at least a portion of the Raman spectrum and the principal component loadings; and
   (d) calculating the polymer property by applying the new principal component score to the regression model.

2. The process of claim 1, wherein the step of obtaining a regression model comprises:
   (i) obtaining a plurality of Raman spectra of samples comprising polyolefins;
   (ii) calculating principal component loadings and principal component scores from the spectra obtained in (i) using principal component analysis (PCA); and
   (iii) forming the regression model using the principal component scores calculated in (ii) such that the regression model correlates the polymer property to the principal component scores.

3. The process of claim 1, wherein the regression model is a locally weighted regression model.

4. The process of claim 1, wherein the polymer property is selected from density, melt flow rate, molecular weight, molecular weight distribution, and functions thereof.

5. The process of claim 1, wherein the sample comprises polyolefin particles.

6. The process of claim 5, wherein the step of acquiring a Raman spectrum comprises:
   (i) providing the sample of polyolefin particles; and
   (ii) irradiating the sample and collecting scattered radiation during a sampling interval using a sampling probe, wherein there is relative motion between the sample and the sampling probe during at least a portion of the sampling interval.

7. The process of claim 1, wherein the polymerization reactor is a fluidized-bed reactor.

8. The process of claim 1, further comprising:
   (i) obtaining a second regression model for determining a second polymer property, the second regression model including second principal component loadings and second principal component scores;
   (ii) calculating a new second principal component score from at least a portion of the Raman spectrum and the second principal component loadings; and
   (iii) calculating the second polymer property by applying the new second principal component score to the second regression model.

9. A process for determining polymer properties in a fluidized-bed reactor system, the process comprising:
   (a) obtaining a locally weighted regression model for determining a polymer property selected from density, melt flow rate, molecular weight, molecular weight distribution, and functions thereof, the locally weighted regression model including principal component loadings and principal component scores;
   (b) acquiring a Raman spectrum of a sample comprising polyolefin particles;
   (c) calculating a new principal component score from at least a portion of the Raman spectrum and the principal component loadings; and
   (d) calculating the polymer property by applying the new principal component score to the locally weighted regression model.

10. The process of claim 9, wherein the step of obtaining a regression model comprises:
    (i) obtaining a plurality of Raman spectra of samples comprising polyolefins;
    (ii) calculating principal component loadings and principal component scores from the spectra obtained in (i) using principal component analysis (PCA); and
    (iii) forming the regression model using the principal component scores calculated in (ii) such that the regression model correlates the polymer property to the principal component scores.

11. The process of claim 9, wherein the step of acquiring a Raman spectrum comprises:
    (i) providing the sample of polyolefin particles; and
    (ii) irradiating the sample and collecting scattered radiation during a sampling interval using a sampling probe, wherein there is relative motion between the sample and the sampling probe during at least a portion of the sampling interval.

12. The process of claim 9, further comprising:
(i) obtaining a second regression model for determining a second polymer property, the second regression model including second principal component loadings and second principal component scores;
(ii) calculating a new second principal component score from at least a portion of the Raman spectrum and the second principal component loadings; and
(iii) calculating the second polymer property by applying the new second principal component score to the second regression model.

13. A process for controlling polymer properties in a polymerization reactor system, the process comprising:
(a) obtaining a regression model for determining a polymer property, the regression model including principal component loadings and principal component scores;
(b) acquiring a Raman spectrum of a sample comprising polyolefin;
(c) calculating a new principal component score from at least a portion of the Raman spectrum and the principal component loadings;
(d) calculating the polymer property by applying the new principal component score to the regression model; and
(e) adjusting at least one polymerization parameter based on the calculated polymer property.

14. The process of claim 13, wherein the step of obtaining a regression model comprises:
(i) obtaining a plurality of Raman spectra of samples comprising polyolefins;
(ii) calculating principal component loadings and principal component scores from the spectra obtained in (i) using principal component analysis (PCA); and
(iii) forming the regression model using the principal component scores calculated in (ii) such that the regression model correlates the polymer property to the principal component scores.

15. The process of claim 13, wherein the regression model is a locally weighted regression model.

16. The process of claim 13, wherein the polymer property is selected from density, melt flow rate, molecular weight, molecular weight distribution, and functions thereof.

17. The process of claim 13, wherein the sample comprises polyolefin particles.

18. The process of claim 17, wherein the step of acquiring a Raman spectrum comprises:
(i) providing the sample of polyolefin particles; and
(ii) irradiating the sample and collecting scattered radiation during a sampling interval using a sampling probe, wherein there is relative motion between the sample and the sampling probe during at least a portion of the sampling interval.

19. The process of claim 13, wherein the polymerization reactor is a fluidized-bed reactor.

20. The process of claim 13, wherein the at least one polymerization parameter is selected from the group consisting of monomer feed rate, comonomer feed rate, catalyst feed rate, hydrogen gas feed rate, and reaction temperature.

21. The process of claim 13, further comprising:
(i) obtaining a second regression model for determining a second polymer property, the second regression model including second principal component loadings and second principal component scores;
(ii) calculating a new second principal component score from at least a portion of the Raman spectrum and the second principal component loadings; and
(iii) calculating the second polymer property by applying the new second principal component score to the second regression model,
and wherein the step of adjusting comprises adjusting at least one polymerization parameter based on the calculated polymer property, the calculated second polymer property, or both calculated polymer properties.

22. A process for controlling polymer properties in a fluidized reactor system, the process comprising:
(a) obtaining a locally weighted regression model for determining a polymer property selected from density, melt flow rate, molecular weight, molecular weight distribution, and functions thereof, the locally weighted regression model including principal component loadings and principal component scores;
(b) acquiring a Raman spectrum of a sample comprising polyolefin particles;
(c) calculating a new principal component score from at least a portion of the Raman spectrum and the principal component loadings;
(d) calculating the polymer property by applying the new principal component score to the locally weighted regression model; and
(e) adjusting at least one polymerization parameter based on the calculated polymer property.

23. The process of claim 22, wherein the step of obtaining a regression model comprises:
(i) obtaining a plurality of Raman spectra of samples comprising polyolefins;
(ii) calculating principal component loadings and principal component scores from the spectra obtained in (i) using principal component analysis (PCA); and
(iii) forming the regression model using the principal component scores calculated in (ii) such that the regression model correlates the polymer property to the principal component scores.

24. The process of claim 22, wherein the step of acquiring a Raman spectrum comprises:
(i) providing the sample of polyolefin particles; and
(ii) irradiating the sample and collecting scattered radiation during a sampling interval using a sampling probe, wherein there is relative motion between the sample and the sampling probe during at least a portion of the sampling interval.

25. The process of claim 22, wherein the at least one polymerization parameter is selected from the group consisting of monomer feed rate, comonomer feed rate, catalyst feed rate, hydrogen gas feed rate, and reaction temperature.

26. The process of claim 22, further comprising:
(i) obtaining a second regression model for determining a second polymer property, the second regression model including second principal component loadings and second principal component scores;
(ii) calculating a new second principal component score from at least a portion of the Raman spectrum and the second principal component loadings; and
(iii) calculating the second polymer property by applying the new second principal component score to the second regression model,
and wherein the step of adjusting comprises adjusting at least one polymerization parameter based on the calculated polymer property, the calculated second polymer property, or both calculated polymer properties.

* * * * *